(12) United States Patent
Funahashi

(10) Patent No.: US 7,642,380 B2
(45) Date of Patent: Jan. 5, 2010

(54) AROMATIC AMINE DERIVATIVE AND ORGANIC ELECTROLUMINESCENCE DEVICE USING THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 132 days.

(21) Appl. No.: 11/681,466

(22) Filed: Mar. 2, 2007

(65) Prior Publication Data

US 2007/0236137 A1  Oct. 11, 2007

(30) Foreign Application Priority Data

Mar. 3, 2006  (JP) .............................. 2006-057257

(51) Int. Cl.
*C07C 211/54* (2006.01)
(52) U.S. Cl. ..................... 564/308; 428/917
(58) Field of Classification Search ................. 564/308
See application file for complete search history.

(56) References Cited

U.S. PATENT DOCUMENTS

| 5,853,905 | A | * | 12/1998 | So et al. ..................... 428/690 |
| 2003/0072966 | A1 | | 4/2003 | Hosokawa et al. |
| 2006/0052641 | A1 | | 3/2006 | Funahashi |
| 2007/0029927 | A1 | | 2/2007 | Kawamura et al. |

FOREIGN PATENT DOCUMENTS

| EP | 1 061 112 A1 | 12/2000 |
| EP | 1 561 794 A1 | 8/2005 |
| JP | 11-154594 | 6/1999 |
| JP | 11-167992 | 6/1999 |
| JP | 11-185965 | 7/1999 |
| JP | 11-185966 | 7/1999 |
| JP | 2001-131541 | 5/2001 |
| JP | 2004-43349 | 2/2004 |
| WO | WO 00/39247 | 7/2000 |
| WO | WO 2004/044088 A1 | 5/2004 |
| WO | WO 2005/091686 A1 | 9/2005 |

OTHER PUBLICATIONS

U.S. Appl. No. 12/368,486, filed Feb. 10, 2009, Funahashi.

* cited by examiner

*Primary Examiner*—Brian J Davis
(74) *Attorney, Agent, or Firm*—Oblon, Spivak, McClelland, Maier & Neustadt, L.L.P.

(57) ABSTRACT

The present invention relates to aromatic amine derivatives having a specific structure; and organic electroluminescent devices comprising a cathode, an anode and one or plural organic thin film layers including at least a light emitting layer which are sandwiched between the cathode and the anode wherein at least one of the organic thin film layers contains the above aromatic amine derivatives in the form of a single substance or a component of a mixture. There are provided the organic electroluminescent devices exhibiting a long life and a high efficiency of light emission which are capable of emitting a blue light having a high color purity, as well as the aromatic amine derivatives capable of realizing such organic electroluminescent devices.

15 Claims, 1 Drawing Sheet

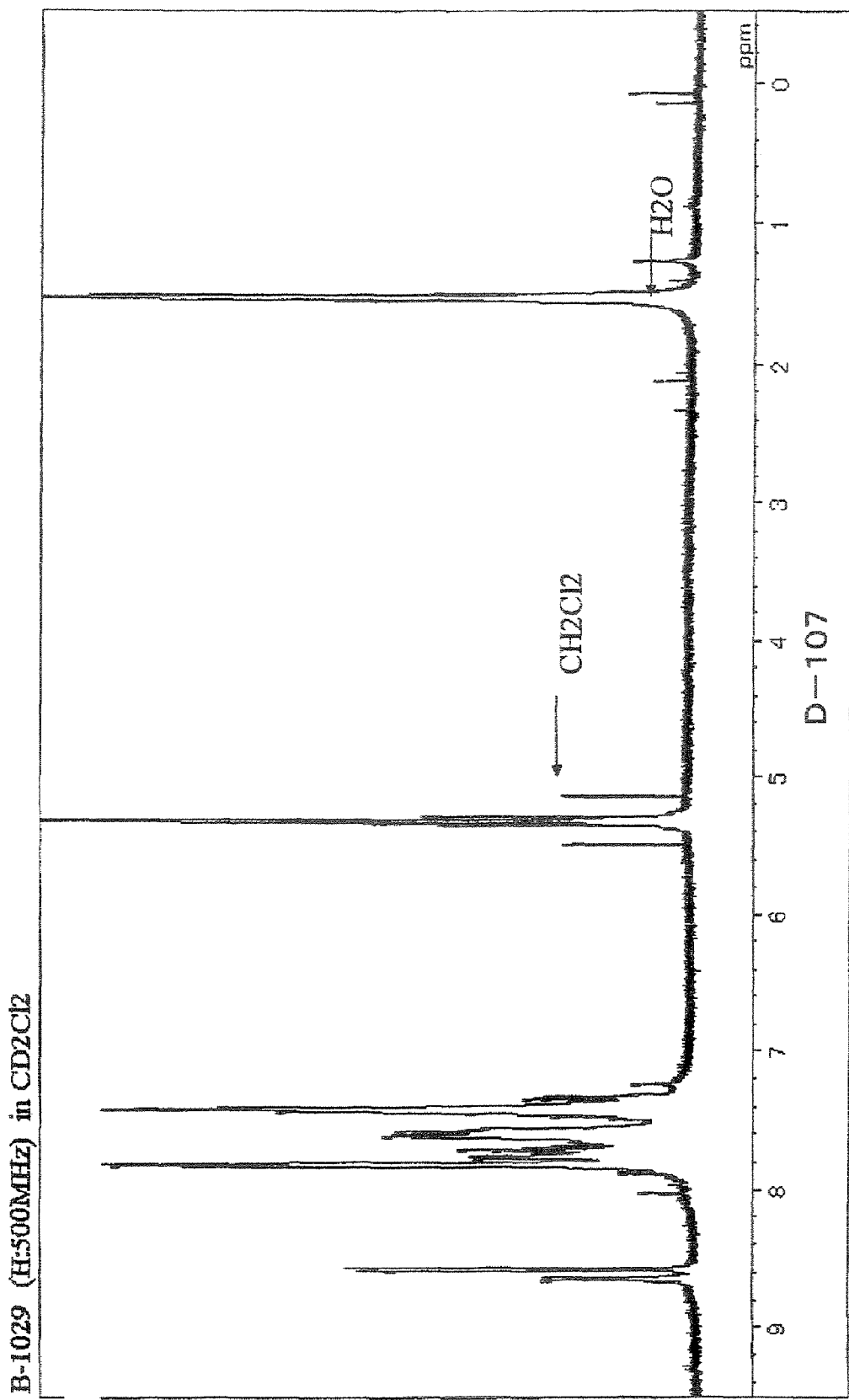

AROMATIC AMINE DERIVATIVE AND ORGANIC ELECTROLUMINESCENCE DEVICE USING THE SAME

TECHNICAL FIELD

The present invention relates to aromatic amine derivatives and organic electroluminescent devices using the same, and more particularly to organic electroluminescent devices which exhibit a high efficiency of light emission and are capable of emitting a blue light having a high color purity, as well as aromatic amine derivatives capable of realizing such electroluminescent devices.

BACKGROUND ART

The organic electroluminescent (EL) devices made by using organic substances have been expected to be applied to production of large area full-color display devices of a solid light emission type at low costs, and have been intensively developed. In general, the organic EL devices are constituted from a light emitting layer and a pair of counter electrodes between which the light emitting layer is sandwiched. In the organic EL devices, when an electric field is applied between the electrodes, electrons are injected from a cathode into the light emitting layer, whereas holes are injected from an anode into the light emitting layer. The electrons and holes injected are recombined in the light emitting layer, so that the light emitting layer is brought into a excited state. When the light emitting layer is returned from the excited state to a ground state, an energy is released in the form of light.

The conventional organic EL devices require a high drive voltage and exhibit a low luminance and a low efficiency of light emission as compared to inorganic light emitting diodes. In addition, the conventional organic EL devices suffer from remarkable deterioration in properties and, therefore, are still practically unusable. Although recently developed organic EL devices are gradually improved to some extent, there is a further demand for developing organic EL devices exhibiting a still higher efficiency of light emission and having a still longer life.

For example, there is disclosed such a technique using a single monoanthracene compound as an organic light-emitting material (JP 11-3782A). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (JP 8-12600A). However, in this technique, an efficiency of light emission obtained by using the material is also as low as about 1 to 3 cd/A. Therefore, further improvement of the technique has been demanded for rendering it practically usable. On the other hand, there have been proposed long-life organic EL devices using a distyryl compound as an organic light-emitting material to which styrylamine, etc., is added (WO 94/006157). However, the organic EL devices still fail to exhibit a sufficiently long life and, therefore, further improvement of these devices has been required.

Further, there are disclosed techniques using a mono- or bis-anthracene compound together with a distyryl compound in an organic light emitting medium layer (JP 2001-284050A). However, in these techniques, the wavelength of emission spectra is too long owing to a conjugated structure of the styryl compound, resulting in poor color purity of light emitted.

In addition, WO 04/044088 discloses a blue light-emitting device using a diaminochrysene derivative. The device is excellent in efficiency of light emission but still fails to show a sufficiently long life and, therefore, further improvement of the device has been required.

DISCLOSURE OF THE INVENTION

Problems to be Solved by the Invention

The present invention has been made to solve the above problems. An object of the present invention is to provide organic EL devices having a long life and a high efficiency of light emission which are capable of emitting a blue light having a high color purity, and aromatic amine derivatives capable of realizing such organic EL devices.

Means for Solving the Problem

As a result of extensive researches for developing aromatic amine derivatives having the above suitable properties and organic EL devices using the aromatic amine derivatives, the inventors have found that the object of the present invention can be achieved by using aromatic amine derivatives represented by the following general formulae (I) in which amino groups are bonded to the 2- and 8-positions of a chrysene skeleton thereof. The present invention has been accomplished on the basis of the above finding.

Thus, the present invention provides an aromatic amine derivative represented by the following general formulae (I):

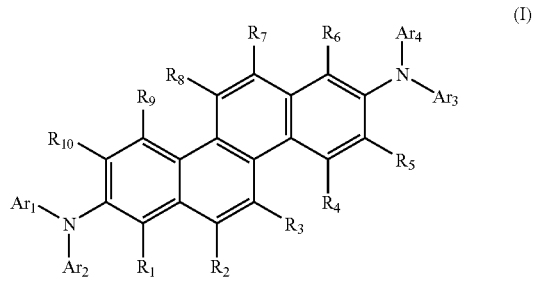

wherein $R_1$ to $R_{10}$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms; and $Ar_1$ to $Ar_4$ are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, or a substituted or unsubstituted heterocyclic group having 5 to 50 ring carbon atoms, with the proviso that when $Ar_1$ to $Ar_4$ are aryl groups, $Ar_1$ and $Ar_2$, and $Ar_3$ and $Ar_4$ may be respectively bonded to each other to form a saturated or unsaturated ring.

Also, the present invention provides an organic electroluminescent device comprising a cathode, an anode and one or plural organic thin film layers including at least a light emitting layer which are sandwiched between the cathode and the anode, wherein at least one of the organic thin film layers contains the above aromatic amine derivative in the form of a single substance or a component of a mixture.

Effect of the Invention

The organic EL device using the aromatic amine derivative according to the present invention can exhibit a practically sufficient luminance of light emitted even upon applying a low voltage thereto, and has a high efficiency of light emission, and the device is free from deterioration in properties even after being used for a long period of time and, therefore, has a long life.

BRIEF DESCRIPTION OF THE DRAWING

FIG. 1 is a view showing $^1$H-NMR spectrum of the compound D-107 as the aromatic amine derivative of the present invention which was obtained in Synthesis Example 1.

PREFERRED EMBODIMENTS FOR CARRYING OUT THE INVENTION

The aromatic amine derivatives of the present invention are compounds represented by the following general formula (I):

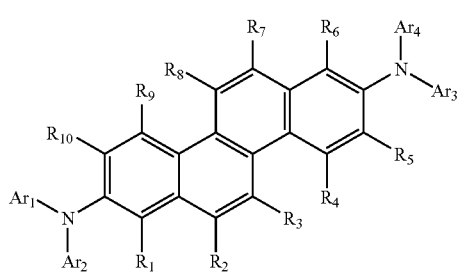

In the general formula (I), $R_1$ to $R_{10}$ are each independently a hydrogen atom, a substituted or unsubstituted alkyl group having 1 to 50 carbon atoms (and preferably 1 to 20 carbon atoms), a substituted or unsubstituted aryl group having 5 to 50 ring carbon atoms (and preferably 5 to 20 ring carbon atoms), a substituted or unsubstituted aralkyl group having 6 to 50 ring carbon atoms (and preferably 6 to 20 ring carbon atoms), a substituted or unsubstituted cycloalkyl group having 3 to 50 ring carbon atoms (and preferably 5 to 12 ring carbon atoms), a substituted or unsubstituted alkoxy group having 1 to 50 carbon atoms (and preferably 1 to 6 carbon atoms), a substituted or unsubstituted aryloxy group having 5 to 50 ring carbon atoms (and preferably 5 to 18 ring carbon atoms), a substituted or unsubstituted arylamino group having 5 to 50 ring carbon atoms (and preferably 5 to 18 ring carbon atoms), a substituted or unsubstituted alkylamino group having 1 to 20 carbon atoms (and preferably 1 to 6 carbon atoms), a substituted or unsubstituted silyl group having 1 to 20 carbon atoms, or a substituted or unsubstituted heterocyclic group having 5 to 50 ring carbon atoms (and preferably 5 to 20 ring carbon atoms).

Examples of the alkyl group as $R_1$ to $R_{10}$ include methyl, ethyl, propyl, isopropyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphneylmethyl and α-benzyloxybenzyl.

Examples of the aryl group as $R_1$ to $R_{10}$ include phenyl, 2-methylphenyl, 3-methylphenyl, 4-methylphenyl, 4-ethylphenyl, biphenyl, 4-methyl biphenyl, 4-ethyl biphenyl, 4-cyclohexyl biphenyl, terphenyl, 3,5-dichlorophenyl, naphthyl, 5-methyl naphthyl, anthryl and pyrenyl.

Examples of the aralkyl group as $R_1$ to $R_{10}$ include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-β-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

Examples of the cycloalkyl group as $R_1$ to $R_{10}$ include cyclopropyl, cyclobutyl, cyclopentyl, cyclohexyl, cycloheptyl, cyclooctyl, cyclononyl, bicycloheptyl, bicyclooctyl, tricyclooctyl and adamantyl. Of these cycloalkyl groups, preferred are cyclopentyl, cyclohexyl, cycloheptyl, bicycloheptyl, bicyclooctyl and adamantyl.

Examples of the alkoxy group as $R_1$ to $R_{10}$ include methoxy, ethoxy, propoxy, isopropoxy, butoxy, isobutoxy, sec-butoxy, tert-butoxy, various pentyloxy groups and various hexyloxy groups.

Examples of the aryloxy group as $R_1$ to $R_{10}$ include phenoxy, tolyloxy and naphthyloxy.

Examples of the arylamino group as $R_1$ to $R_{10}$ include diphenylamino, ditolylamino, dinaphthylamino and naphthylphenylamino.

Examples of the alkylamino group as $R_1$ to $R_{10}$ include dimethylamino, diethylamino and dihexylamino.

Examples of the heterocyclic group as $R_1$ to $R_{10}$ include residues of imidazole, benzoimidazole, pyrrole, furan, thiophene, benzothiophene, oxadiazoline, indoline, carbazole, pyridine, quinoline, isoquinoline, benzoquinone, pyrazine, imidazoline, piperidine, etc.

Examples of the substituent groups which may be bonded to $R_1$ to $R_{10}$ include a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group, a halogen atom, a cyano group, a nitro group, a hydroxyl group and a carboxyl group.

In the general formula (I), among the $R_1$ to $R_{10}$ groups, $R_2$ and/or $R_7$, or $R_3$ and/or $R_8$, are preferably any of the above exemplified groups other than a hydrogen atom.

In the general formula (I), $Ar_1$ to $Ar_4$ are each independently a substituted or unsubstituted alkyl group having 1 to 50 carbon atoms (and preferably 1 to 20 carbon atoms), a substituted or unsubstituted aryl group having 5 to 50 ring carbon atoms (and preferably 5 to 20 ring carbon atoms), a substituted or unsubstituted aralkyl group having 6 to 50 ring carbon atoms (and preferably 6 to 20 ring carbon atoms), a substituted or unsubstituted cycloalkyl group having 3 to 50 ring carbon atoms (and preferably 5 to 12 ring carbon atoms), or a substituted or unsubstituted heterocyclic group having 5 to 50 ring carbon atoms (and preferably 5 to 20 ring carbon atoms).

Specific examples of the above respective groups as $Ar_1$ to $Ar_4$ are the same as those described above for $R_1$ to $R_{10}$. Also, specific examples of the substituent groups which may be bonded to the above respective group as $Ar_1$ to $Ar_4$ are the same as those described above for $R_1$ to $R_{10}$.

In the general formula (I), when $Ar_1$ to $Ar_4$ are aryl groups, $Ar_1$ and $Ar_2$, and $Ar_3$ and $Ar_4$ may be respectively bonded to each other to form a saturated or unsaturated ring.

Examples of the saturated or unsaturated ring include cycloalkane rings having 4 to 12 ring carbon atoms such as cyclobutane, cyclopentane, cyclohexane, adamantane and norbornane; cycloalkene rings having 4 to 12 ring carbon atoms such as cyclobutene, cyclopentene, cyclohexene, cycloheptene and cyclooctene; cycloalkadiene rings having 6 to 12 ring carbon atoms such as cyclohexadiene, cycloheptadiene and cyclooctadiene; aromatic rings having 6 to 50 ring carbon atoms such as benzene, naphthalene, phenanthrene, anthracene, pyrene, chrysene and acenaphthylene; and heterocyclic rings having 5 to 50 ring carbon atoms such as imidazole, pyrrole, furan, thiophene and pyridine.

The aromatic amine derivatives represented by the general formula (I) are preferably compounds represented by the following general formula (II):

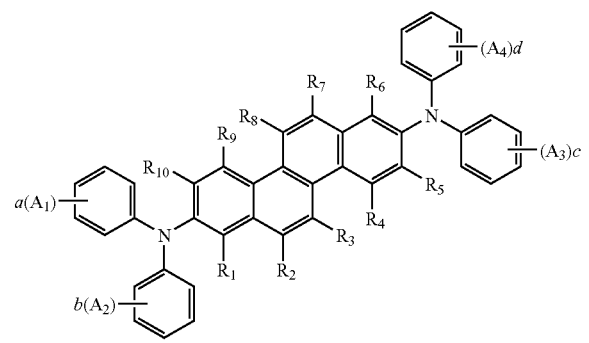

(II)

In the general formula (II), $R_1$ to $R_{10}$ are each independently the same as those described above in the general formula (I). In the general formula (II), among the $R_1$ to $R_{10}$ groups, $R_2$ and/or $R_7$, or $R_3$ and/or $R_8$, are preferably any of the above exemplified groups other than a hydrogen atom.

In the general formula (II), $A_1$ to $A_4$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, a substituted or unsubstituted heterocyclic group having 5 to 50 ring carbon atoms, or a halogen atom.

Specific examples of the above respective groups other than a halogen atom as $A_1$ to $A_4$ in the general formula (II) are the same as those described above for $R_1$ to $R_{10}$, and specific examples of the substituent groups which may be bonded to these groups are also the same as those described above for $R_1$ to $R_{10}$. Specific examples of the halogen atom include fluorine, chlorine, bromine, etc.

In the general formula (II), a, b, c and d are each independently an integer of 0 to 5. When a, b, c and d are respectively an integer of 2 or more, plural groups of each of $A_1$ to $A_4$ may be the same or different and bonded to each other to form a saturated or unsaturated ring. Also, $A_1$ and $A_2$, and $A_3$ and $A_4$ may be respectively bonded to each other to form a saturated or unsaturated ring.

Examples of the saturated or unsaturated ring are the same as those described above for $Ar_1$ to $Ar_4$ in the general formula (I).

Specific examples of the aromatic amine derivatives represented by the general formula (I) include the following compounds enumerated below, though not particularly limited thereto. Meanwhile, in the following compounds, Me represents a methyl group.

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-1 | —Me | —Me | —Me | —Me | H | H | H | H | H | H | H | H | H | H |
| D-2 | —Me | —CH(Me)₂ | —Me | —CH(Me)₂ | H | H | H | H | H | H | H | H | H | H |
| D-3 | —CH(Me)₂ | —CH(Me)₂ | —CH(Me)₂ | —CH(Me)₂ | H | H | H | H | H | H | H | H | H | H |
| D-4 | —CH₂CH₃ | —CH(Me)₂ | —CH(Me)₂ | —Me | H | H | H | H | H | H | H | H | H | H |
| D-5 | —C(Me)₃ | —C(Me)₃ | —C(Me)₃ | —C(Me)₃ | H | —Me | H | H | H | H | —Me | H | H | H |
| D-6 | —C(Me)₃ | —C(Me)₃ | —C(Me)₃ | —C(Me)₃ | H | —Me | —Me | H | H | H | —Me | —Me | H | H |
| D-7 | —CH(Me)₂ | —CH(Me)₂ | —CH(Me)₂ | —CH(Me)₂ | H | —Me | H | H | H | H | —Me | H | H | H |
| D-8 | —Me | —CH(Me)₂ | —Me | —CH(Me)₂ | H | —CH(Me)₂ | H | H | H | H | —CH(Me)₂ | H | H | H |
| D-9 | —(CH₂)₄CH₃ | —(CH₂)₄CH₃ | —(CH₂)₄CH₃ | —(CH₂)₄CH₃ | H | H | H | H | H | H | H | H | H | H |
| D-10 | —C(Me)₃ | —C(Me)₃ | —C(Me)₃ | —C(Me)₃ | H | —Ph | H | H | H | H | —Ph | H | H | H |

-continued

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-11 | —Me | cyclohexyl | —Me | cyclohexyl | H | H | H | H | H | H | H | H | H | H |
| D-12 | cyclohexyl | cyclohexyl | cyclohexyl | cyclohexyl | H | H | H | H | H | H | H | H | H | H |
| D-13 | —Me | phenyl | —Me | phenyl | H | H | H | H | H | H | H | H | H | H |
| D-14 | iPr | phenyl | iPr | phenyl | H | H | H | H | H | H | H | H | H | H |
| D-15 | tBu | 9,9-dimethylfluorenyl | tBu | 9,9-dimethylfluorenyl | H | H | H | H | H | H | H | H | H | H |
| D-16 | tBu | CMe2Ph (on phenyl) | tBu | CMe2Ph (on phenyl) | H | H | H | H | H | H | H | H | H | H |
| D-17 | iPr | CMe2 (phenyl) | iPr | CMe2 (phenyl) | H | H | H | H | H | H | Me | H | H | H |
| D-18 | —Me | CMe3-phenyl | —Me | CMe3-phenyl | H | Me | Me | H | H | H | Me | Me | H | H |
| D-19 | tBu | tetrahydronaphthyl | tBu | tetrahydronaphthyl | H | Me | H | H | H | H | Me | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-20 | tBu | 4-F-C₆H₄ | tBu | 4-F-C₆H₄ | H | Me | H | H | H | H | Me | H | H | H |
| D-21 | Me | 4-pyridyl | Me | 4-pyridyl | H | H | H | H | H | H | H | H | H | H |
| D-22 | cyclohexyl | isoquinolinyl | cyclohexyl | isoquinolinyl | H | H | H | H | H | H | H | H | H | H |
| D-23 | Me | 2-pyridyl | Me | 2-pyridyl | H | H | H | H | H | H | H | H | H | H |
| D-24 | iPr | quinolinyl | iPr | quinolinyl | H | H | H | H | H | H | H | H | H | H |
| D-25 | tBu | 5-Me-2-thienyl | tBu | 5-Me-2-thienyl | H | H | H | H | H | H | H | H | H | H |
| D-26 | iPr | 4-pyridyl | iPr | 4-pyridyl | H | H | H | H | H | H | H | H | H | H |
| D-27 | iPr | 2-pyridyl | iPr | 2-pyridyl | H | H | H | H | H | H | H | H | H | H |
| D-28 | Me | isochromanyl | Me | isochromanyl | H | Me | H | H | H | H | Me | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-29 | iPr | 3-pyridyl | iPr | 3-pyridyl | H | H | H | H | H | H | H | H | H | H |
| D-30 | tBu | quinoxalinyl | tBu | quinoxalinyl | H | H | H | H | H | H | H | H | H | H |
| D-31 | Ph | 3-pyridyl | Ph | 3-pyridyl | H | H | H | H | H | H | H | H | H | H |
| D-32 | Ph | 4-pyridyl | Ph | 4-pyridyl | H | H | H | H | H | H | H | H | H | H |
| D-33 | Ph | 3-pyridyl (N adjacent) | Ph | 3-pyridyl (N adjacent) | H | H | H | H | H | H | H | H | H | H |
| D-34 | 4-MeC₆H₄ | 3-pyridyl | 4-MeC₆H₄ | 3-pyridyl | H | H | H | H | H | H | H | H | H | H |
| D-35 | 4-MeC₆H₄ | 3-pyridyl | 4-MeC₆H₄ | 3-pyridyl | H | H | H | H | H | H | H | H | H | H |
| D-36 | 4-MeC₆H₄ | 2-pyridyl | 4-MeC₆H₄ | 2-pyridyl | H | H | H | H | H | H | H | H | H | H |
| D-37 | 4-iPrC₆H₄ | 4-pyridyl | 4-iPrC₆H₄ | 4-pyridyl | H | H | H | H | H | H | H | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-38 | 4-(CHMe₂)phenyl | 3-pyridyl | 4-(CHMe₂)phenyl | 3-pyridyl | H | H | H | H | H | H | H | H | H | H |
| D-39 | 4-(CHMe₂)phenyl | 2-pyridyl | 4-(CHMe₂)phenyl | 2-pyridyl | H | H | H | H | H | H | H | H | H | H |
| D-40 | 4-(CHMe₂)phenyl | 3-pyridyl | 4-(CHMe₂)phenyl | 3-pyridyl | H | —Me | H | H | H | H | H | H | H | H |
| D-41 | 4-(CMe₃)phenyl | 4-pyridyl | 4-(CMe₃)phenyl | 4-pyridyl | H | H | H | H | H | H | H | H | H | H |
| D-42 | 4-(CMe₃)phenyl | 3-pyridyl | 4-(CMe₃)phenyl | 3-pyridyl | H | H | H | H | H | H | H | H | H | H |
| D-43 | 4-(CMe₃)phenyl | 3-pyridyl | 4-(CMe₃)phenyl | 3-pyridyl | H | H | H | H | H | H | H | H | H | H |
| D-44 | 2-naphthyl | 3-pyridyl | 2-naphthyl | 3-pyridyl | H | H | H | H | H | H | H | H | H | H |
| D-45 | 2-naphthyl | 3-pyridyl | 2-naphthyl | 3-pyridyl | H | H | H | H | H | H | H | H | H | H |
| D-46 | 2-naphthyl | 2-pyridyl | 2-naphthyl | 2-pyridyl | H | H | H | H | H | H | H | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-47 | 3,5-diMe-phenyl | 4-pyridyl | 3,5-diMe-phenyl | 4-pyridyl | H | H | H | H | H | H | H | H | H | H |
| D-48 | 3,5-diMe-phenyl | 3-pyridyl | 3,5-diMe-phenyl | 3-pyridyl | H | H | H | H | H | H | H | H | H | H |
| D-49 | 3,5-diMe-phenyl | 2-pyridyl | 3,5-diMe-phenyl | 2-pyridyl | H | H | H | H | H | H | H | H | H | H |
| D-50 | 3,5-diMe-phenyl | 3-pyridyl | 3,5-diMe-phenyl | 3-pyridyl | H | Me | H | H | H | H | Me | H | H | H |
| D-51 | 2,6-diMe-phenyl | 4-pyridyl | 2,6-diMe-phenyl | 4-pyridyl | H | H | H | H | H | H | H | H | H | H |
| D-52 | 2,6-diMe-phenyl | 3-pyridyl | 2,6-diMe-phenyl | 3-pyridyl | H | H | H | H | H | H | H | H | H | H |
| D-53 | 2,6-diMe-phenyl | 2-pyridyl | 2,6-diMe-phenyl | 2-pyridyl | H | H | H | H | H | H | H | H | H | H |

-continued

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-54 | 2,4-dimethylphenyl | 4-pyridyl | 2,4-dimethylphenyl | 4-pyridyl | H | H | H | H | H | H | H | H | H | H |
| D-55 | 2,4-dimethylphenyl | 3-pyridyl | 2,4-dimethylphenyl | 3-pyridyl | H | H | H | H | H | H | H | H | H | H |
| D-56 | 2,4-dimethylphenyl | 2-pyridyl | 2,4-dimethylphenyl | 2-pyridyl | H | H | H | H | H | H | H | H | H | H |
| D-57 | 5,6,7,8-tetrahydronaphthyl | 4-pyridyl | 5,6,7,8-tetrahydronaphthyl | 4-pyridyl | H | H | H | H | H | H | H | H | H | H |
| D-58 | 5,6,7,8-tetrahydronaphthyl | 3-pyridyl | 5,6,7,8-tetrahydronaphthyl | 3-pyridyl | H | H | H | H | H | H | H | H | H | H |
| D-59 | 5,6,7,8-tetrahydronaphthyl | 2-pyridyl | 5,6,7,8-tetrahydronaphthyl | 2-pyridyl | H | H | H | H | H | H | H | H | H | H |
| D-60 | 5,6,7,8-tetrahydronaphthyl | 3-pyridyl | 5,6,7,8-tetrahydronaphthyl | 3-pyridyl | H | Me | H | H | H | H | Me | H | H | H |
| D-61 | phenyl | isoquinolyl | phenyl | isoquinolyl | H | H | H | H | H | H | H | H | H | H |
| D-62 | phenyl | quinolyl | phenyl | quinolyl | H | H | H | H | H | H | H | H | H | H |

-continued
| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-63 |  |  | 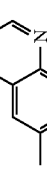 | 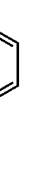 | H | H | H | H | H | H | H | H | H | H |
| D-64 |  |  | 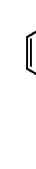 | 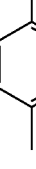 | H | H | H | H | H | H | H | H | H | H |
| D-65 |  |  | 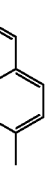 |  | H | H | H | H | H | H | H | H | H | H |
| D-66 |  | 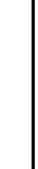 | 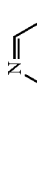 |  | H | H | H | H | H | H | H | H | H | H |
| D-67 |  | 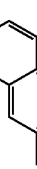 | 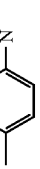 |  | H | H | H | H | H | H | H | H | H | H |
| D-68 |  |  | 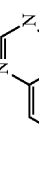 | 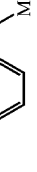 | H | Me | H | H | H | H | Me | H | H | H |
| D-69 |  | 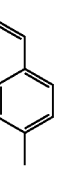 | 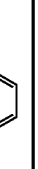 |  | H | H | H | H | H | H | H | H | H | H |
| D-70 |  | 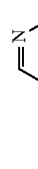 | 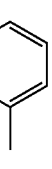 |  | H | H | H | H | H | H | H | H | H | H |

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-71 | 4-pyridyl | 4-pyridyl | 4-pyridyl | 4-pyridyl | H | H | H | H | H | H | H | H | H | H |
| D-72 | 3-pyridyl | 3-pyridyl | 3-pyridyl | 3-pyridyl | H | H | H | H | H | H | H | H | H | H |
| D-73 | 2-pyridyl | 2-pyridyl | 2-pyridyl | 2-pyridyl | H | H | H | H | H | H | H | H | H | H |
| D-74 | 4-pyridyl | 4-pyridyl | 4-pyridyl | 4-pyridyl | H | H | H | H | H | H | H | H | H | H |
| D-75 | 3-pyridyl | 3-pyridyl | 3-pyridyl | 3-pyridyl | H | H | H | H | H | H | H | H | H | H |
| D-76 | 2-pyridyl | 2-pyridyl | 2-pyridyl | 2-pyridyl | H | H | H | H | H | H | H | H | H | H |
| D-77 | quinazolinyl | 4-pyridyl | quinazolinyl | 4-pyridyl | H | H | H | H | H | H | H | H | H | H |
| D-78 | quinazolinyl | 3-pyridyl | quinazolinyl | 3-pyridyl | H | H | H | H | H | H | H | H | H | H |
| D-79 | quinazolinyl | 2-pyridyl | quinazolinyl | 2-pyridyl | H | H | H | H | H | H | H | H | H | H |

-continued
| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-80 | 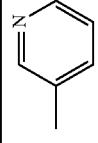 |  | 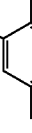 |  | H | —Me | H | H | H | H | —Me | H | H | H |
| D-81 | 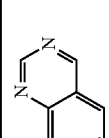 |  |  |  | H | H | H | H | H | H | H | H | H | H |
| D-82 |  |  |  |  | H | H | H | H | H | H | H | H | H | H |
| D-83 | 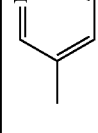 |  | 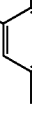 |  | H | H | H | H | H | H | H | H | H | H |
| D-84 | 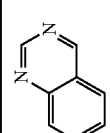 |  |  |  | H | H | H | H | H | H | H | H | H | H |
| D-85 | 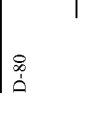 | 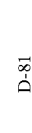 |  |  | H | H | H | H | H | H | H | H | H | H |
| D-86 |  |  | | | H | H | H | H | H | H | H | H | H | H |
| D-87 | | | | | H | H | H | H | H | H | H | H | H | H |
| D-88 |  |  | | | H | Me | H | H | H | H | Me | H | H | H |

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-89 | 2-pyridyl | quinoxalinyl | 2-pyridyl | quinoxalinyl | H | H | H | H | H | H | H | H | H | H |
| D-90 | 4-pyridyl | quinoxalinyl | 4-pyridyl | quinoxalinyl | H | H | H | H | H | H | H | H | H | H |
| D-91 | Ph | Ph | Ph | Ph | H | H | H | H | H | H | H | H | H | H |
| D-92 | Ph | 3-MePh | Ph | 3-MePh | H | H | H | H | H | H | H | H | H | H |
| D-93 | 3-MePh | 3-MePh | 3-MePh | 3-MePh | H | H | H | H | H | H | H | H | H | H |
| D-94 | Ph | 4-MePh | Ph | 4-MePh | H | H | H | H | H | H | H | H | H | H |
| D-95 | 2,3-diMePh | 2,3-diMePh | 2,3-diMePh | 2,3-diMePh | H | H | H | H | H | H | H | H | H | H |
| D-96 | 2,4,6-triMePh | 2,4,6-triMePh | 2,4,6-triMePh | 2,4,6-triMePh | H | H | H | H | H | H | H | H | H | H |
| D-97 | 4-MePh | 4-MePh | 4-MePh | 4-MePh | H | H | H | H | H | H | H | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-98 | 4-cumyl-phenyl | 3,5-dimethylphenyl | 4-cumyl-phenyl | 3,5-dimethylphenyl | H | H | H | H | H | H | H | H | H | H |
| D-99 | 4-cumyl-phenyl | 4-cumyl-phenyl | 4-cumyl-phenyl | 4-cumyl-phenyl | H | H | H | H | H | H | H | H | H | H |
| D-100 | 4-tert-butyl-phenyl | 4-tert-butyl-phenyl | 4-tert-butyl-phenyl | 4-tert-butyl-phenyl | H | H | H | H | H | H | H | H | H | H |
| D-101 | phenyl | 4-methylphenyl | phenyl | 4-cumyl-phenyl | H | H | H | H | H | H | H | H | H | H |
| D-102 | 4-methylphenyl | 4-methylphenyl | 4-methylphenyl | 4-cumyl-phenyl | H | H | H | H | H | H | H | H | H | H |
| D-103 | 4-cumyl-phenyl | 4-cyclohexyl-phenyl | 4-cumyl-phenyl | 4-cyclohexyl-phenyl | H | H | H | H | H | H | H | H | H | H |
| D-104 | 3,5-dimethylphenyl | 3,5-dimethylphenyl | 3,5-dimethylphenyl | 3,5-dimethylphenyl | H | H | H | H | H | H | H | H | H | H |
| D-105 | phenyl | biphenyl | phenyl | biphenyl | H | H | H | H | H | H | H | H | H | H |
| D-106 | phenyl | 2-naphthyl | phenyl | 2-naphthyl | H | H | H | H | H | H | H | H | H | H |
| D-107 | 2-naphthyl | 2-naphthyl | 2-naphthyl | 2-naphthyl | H | H | H | H | H | H | H | H | H | H |

-continued
| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-108 |  |  |  |  | H | H | H | H | H | H | H | H | H | H |
| D-109 |  |  |  |  | H | H | H | H | H | H | H | H | H | H |
| D-110 |  |  |  |  | H | H | H | H | H | H | H | H | H | H |
| D-111 |  |  |  |  | H | H | H | H | H | H | H | H | H | H |
| D-112 |  |  |  |  | H | H | H | H | H | H | H | H | H | H |
| D-113 |  |  |  |  | H | H | H | H | H | H | H | H | H | H |
| D-114 |  |  |  |  | H | H | H | H | H | H | H | H | H | H |
| D-115 |  |  |  |  | H | H | H | H | H | H | H | H | H | H |
| D-116 |  |  |  |  | H | H | H | H | H | H | H | H | H | H |

-continued

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-117 | 6-Me-naphth-2-yl | 4-(CMe2H)-phenyl | 6-Me-naphth-2-yl | 4-(CMe2H)-phenyl | H | H | H | H | H | H | H | H | H | H |
| D-118 | 4-cyclohexyl-phenyl | 4-cyclohexyl-phenyl | 4-cyclohexyl-phenyl | 4-cyclohexyl-phenyl | H | H | H | H | H | H | H | H | H | H |
| D-119 | 4-cyclohexyl-phenyl | 6-tetralin-2-yl | 4-cyclohexyl-phenyl | 6-tetralin-2-yl | H | H | H | H | H | H | H | H | H | H |
| D-120 | 9,9-dimethylfluoren-2-yl | 9,9-dimethylfluoren-2-yl | 9,9-dimethylfluoren-2-yl | 9,9-dimethylfluoren-2-yl | H | H | H | H | H | H | H | H | H | H |
| D-121 | 9,9-dimethylfluoren-2-yl | phenyl | 9,9-dimethylfluoren-2-yl | phenyl | H | H | H | H | H | H | H | H | H | H |
| D-122 | 4-(CMePh2)-phenyl | 4-(CMePh2)-phenyl | 4-(CMe2H)-phenyl | 4-(CMePh2)-phenyl | H | H | H | H | H | H | H | H | H | H |
| D-123 | pentafluorophenyl | phenyl | pentafluorophenyl | phenyl | H | H | H | H | H | H | H | H | H | H |
| D-124 | 3,5-dimethylphenyl | 4-(CMe2H)-phenyl | 3,5-dimethylphenyl | 4-(CMe2H)-phenyl | H | H | H | H | H | H | H | H | H | H |

-continued

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-125 | 9-phenanthryl | phenyl | 9-phenanthryl | phenyl | H | H | H | H | H | H | H | H | H | H |
| D-126 | 3,5-dicyclohexylphenyl | 4-cyclohexylphenyl | 3,5-dicyclohexylphenyl | 4-cyclohexylphenyl | H | H | H | H | H | H | H | H | H | H |
| D-127 | phenyl | 4-(trimethylsilyl)phenyl | phenyl | 4-(trimethylsilyl)phenyl | H | H | H | H | H | H | H | H | H | H |
| D-128 | phenyl | 4-(dimethylamino)phenyl | phenyl | 4-(dimethylamino)phenyl | H | H | H | H | H | H | H | H | H | H |
| D-129 | phenyl | 4-(diphenylamino)phenyl | phenyl | 4-(diphenylamino)phenyl | H | H | H | H | H | H | H | H | H | H |
| D-130 | 4-(trimethylsilyl)phenyl | 4-(trimethylsilyl)phenyl | 4-(trimethylsilyl)phenyl | 4-(trimethylsilyl)phenyl | H | H | H | H | H | H | H | H | H | H |
| D-131 | phenyl | phenyl | phenyl | phenyl | H | H | H | H | H | H | H | Me | Me | H |
| D-132 | 3-methylphenyl | 3-methylphenyl | 3-methylphenyl | 3-methylphenyl | H | H | Me | Me | H | H | H | Me | Me | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-133 | 4-MeC₆H₄ | 4-MeC₆H₄ | 4-MeC₆H₄ | 4-MeC₆H₄ | H | H | Me | H | H | H | H | Me | H | H |
| D-134 | 4-tBuC₆H₄ | 4-tBuC₆H₄ | 4-tBuC₆H₄ | 4-tBuC₆H₄ | H | H | Me | H | H | H | H | Me | H | H |
| D-135 | 2,4-Me₂C₆H₃ | 3,5-Me₂C₆H₃ | 2,4-Me₂C₆H₃ | 3,5-Me₂C₆H₃ | H | H | Me | H | H | H | H | Me | H | H |
| D-136 | 2,4,6-Me₃C₆H₂ | 2,4,6-Me₃C₆H₂ | 2,4,6-Me₃C₆H₂ | 2,4,6-Me₃C₆H₂ | H | H | Me | H | H | H | H | Me | H | H |
| D-137 | 4-(iPr)C₆H₄ | 4-MeC₆H₄ | 2,4,6-Me₃C₆H₂ | 4-(iPr)C₆H₄ | H | H | Me | H | H | H | H | Me | H | H |
| D-138 | 4-CyC₆H₄ | 4-CyC₆H₄ | 4-MeC₆H₄ | 4-CyC₆H₄ | H | H | Me | H | H | H | H | Me | H | H |
| D-139 | 2-Naphthyl | 2-Naphthyl | 2-Naphthyl | 2-Naphthyl | H | H | Me | H | H | H | H | Me | H | H |
| D-140 | 4-PhC₆H₄ | 4-PhC₆H₄ | 4-PhC₆H₄ | 4-PhC₆H₄ | H | H | Me | H | H | H | H | Me | H | H |
| D-141 | Ph | Ph | Ph | Ph | H | Me | H | H | H | H | Me | H | H | H |

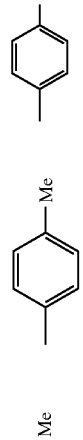

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-142 | 3-Me-C₆H₄ | 3-Me-C₆H₄ | 3-Me-C₆H₄ | 3-Me-C₆H₄ | H | -Me | H | H | H | H | -Me | H | H | H |
| D-143 | 4-Me-C₆H₄ | 4-Me-C₆H₄ | 4-Me-C₆H₄ | 4-Me-C₆H₄ | H | -Me | H | H | H | H | -Me | H | H | H |
| D-144 | 4-tBu-C₆H₄ | 4-tBu-C₆H₄ | 4-tBu-C₆H₄ | 4-tBu-C₆H₄ | H | -Me | H | H | H | H | -Me | H | H | H |
| D-145 | 2,4-diMe-C₆H₃ | 3,5-diMe-C₆H₃ | 2,4-diMe-C₆H₃ | 3,5-diMe-C₆H₃ | H | -Me | H | H | H | H | -Me | H | H | H |
| D-146 | 2,4,6-triMe-C₆H₂ | 2,4,6-triMe-C₆H₂ | 2,4,6-triMe-C₆H₂ | 2,4,6-triMe-C₆H₂ | H | -Me | H | H | H | H | -Me | H | H | H |
| D-147 | 4-iPr-C₆H₄ | 4-iPr-C₆H₄ | 4-iPr-C₆H₄ | 4-iPr-C₆H₄ | H | -Me | H | H | H | H | -Me | H | H | H |
| D-148 | Naphthyl | 4-Cyclohexyl-C₆H₄ | 4-Cyclohexyl-C₆H₄ | 4-Cyclohexyl-C₆H₄ | H | -Me | H | H | H | H | -Me | H | H | H |
| D-149 | Naphthyl | Naphthyl | Naphthyl | Naphthyl | H | -Me | H | H | H | H | -Me | H | H | H |
| D-150 | Biphenyl | Biphenyl | Biphenyl | Biphenyl | H | -Me | H | H | H | H | -Me | H | H | H |

-continued

| No | Ar1 | Ar2 | Ar3 | Ar4 | R1 | R2 | R3 | R4 | R5 | R6 | R7 | R8 | R9 | R10 |
|---|---|---|---|---|---|---|---|---|---|---|---|---|---|---|
| D-151 | Ph | Ph | Ph | Ph | H | iPr | H | H | H | H | iPr | H | H | H |
| D-152 | Ph | 3-MeC6H4 | Ph | 3-MeC6H4 | H | iPr | H | H | H | H | iPr | H | H | H |
| D-153 | 3-MeC6H4 | 3-MeC6H4 | 3-MeC6H4 | 3-MeC6H4 | H | iPr | H | H | H | H | iPr | H | H | H |
| D-154 | Ph | 4-MeC6H4 | Ph | 4-MeC6H4 | H | iPr | H | H | H | H | iPr | H | H | H |
| D-155 | 2,4-Me2C6H3 | 2,4-Me2C6H3 | 2,4-Me2C6H3 | 2,4-Me2C6H3 | H | iPr | H | H | H | H | iPr | H | H | H |
| D-156 | 2,4,6-Me3C6H2 | 2,4,6-Me3C6H2 | 2,4,6-Me3C6H2 | 2,4,6-Me3C6H2 | H | iPr | H | H | H | H | iPr | H | H | H |
| D-157 | 4-MeC6H4 | Ph | Ph | 4-MeC6H4 | H | iPr | H | H | H | H | iPr | H | H | H |
| D-158 | 4-iPrC6H4 | 3,5-Me2C6H3 | 4-iPrC6H4 | 3,5-Me2C6H3 | H | iPr | H | H | H | H | iPr | H | H | H |

-continued

| No | Ar1 | Ar2 | Ar3 | Ar4 | R₁ | R₂ | R₃ | R₄ | R₅ | R₆ | R₇ | R₈ | R₉ | R₁₀ |
|---|---|---|---|---|---|---|---|---|---|---|---|---|---|---|
| D-159 | 4-CHMe₂-C₆H₄ | 4-CHMe₂-C₆H₄ | 4-CHMe₂-C₆H₄ | 4-CHMe₂-C₆H₄ | —H | CHMe₂ | —H | —H | —H | —H | CHMe₂ | —H | —H | —H |
| D-160 | 4-CMe₃-C₆H₄ | 4-CMe₃-C₆H₄ | 4-CMe₃-C₆H₄ | 4-CMe₃-C₆H₄ | —H | CHMe₂ | —H | —H | —H | —H | CHMe₂ | —H | —H | —H |

| No | Ar1 | Ar2 | Ar3 |
|---|---|---|---|
| D-161 | 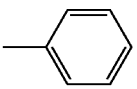 | 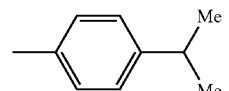 | 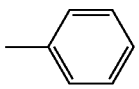 |
| D-162 |  | 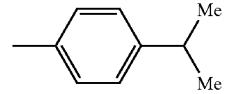 | 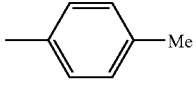 |
| D-163 | 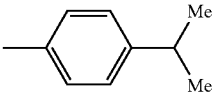 | 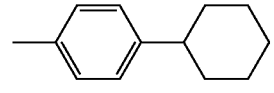 | 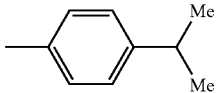 |
| D-164 | 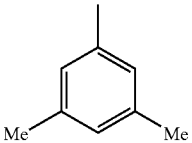 | 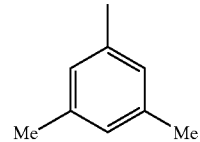 | 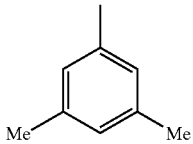 |
| D-165 | 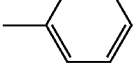 | 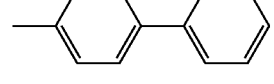 | 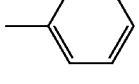 |
| D-166 | 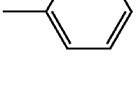 | 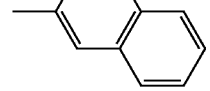 | 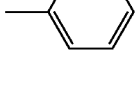 |
| D-167 | 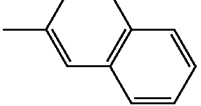 | 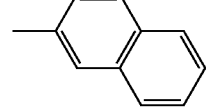 | 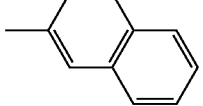 |
| D-168 | 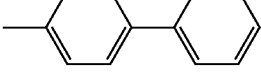 | 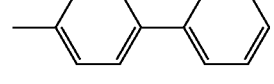 | 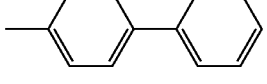 |
| D-169 | 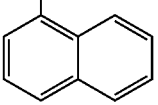 | 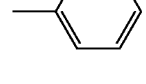 | 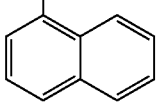 |
| D-170 | 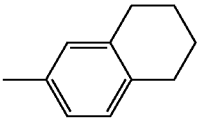 | 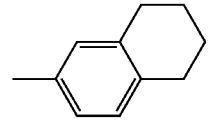 | 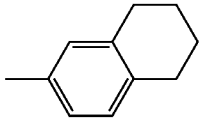 |
| D-171 | 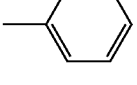 | 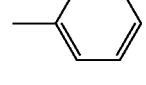 | 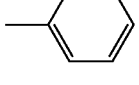 |
| D-172 | 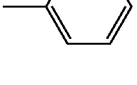 | 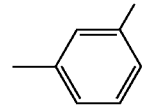 | 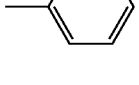 |

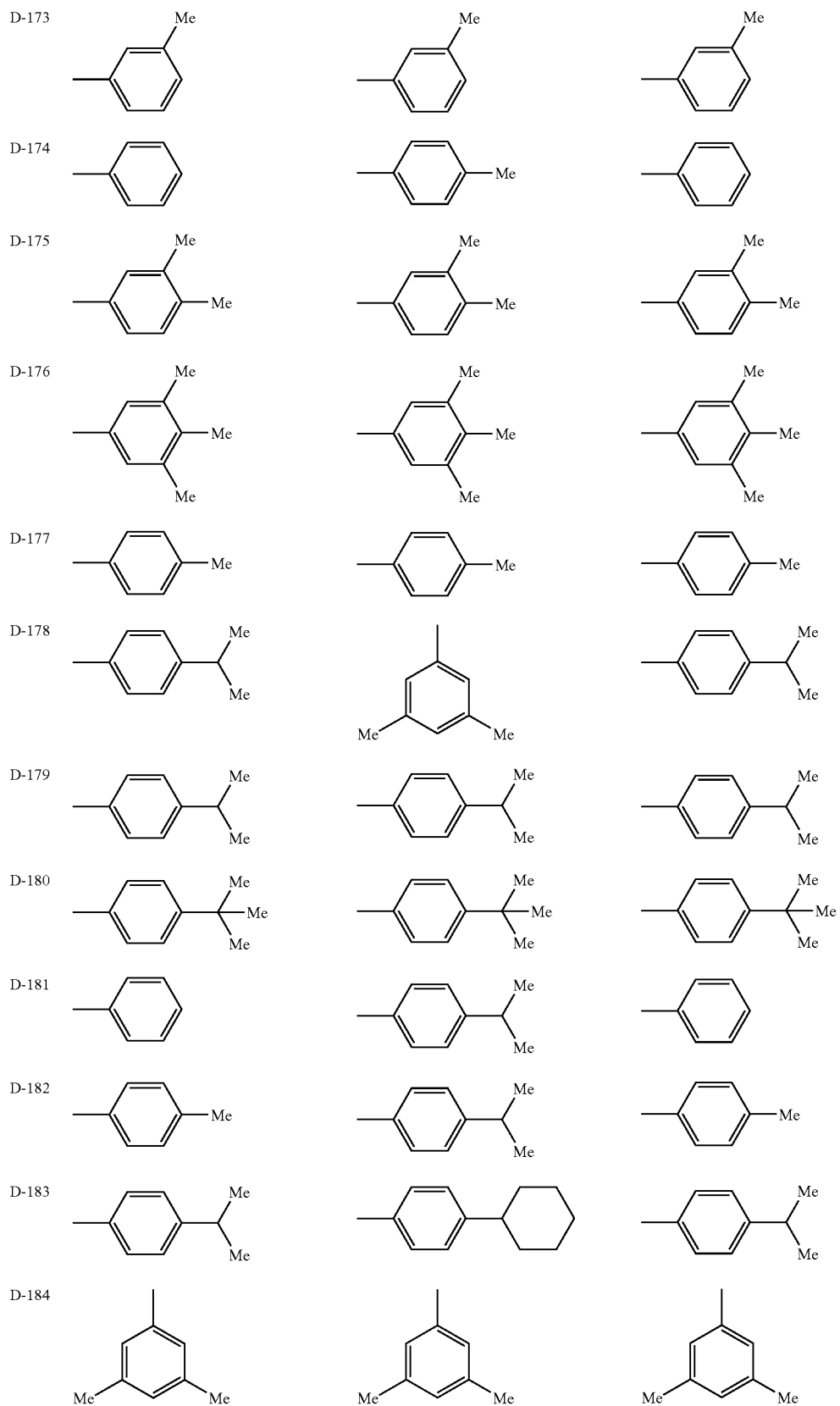

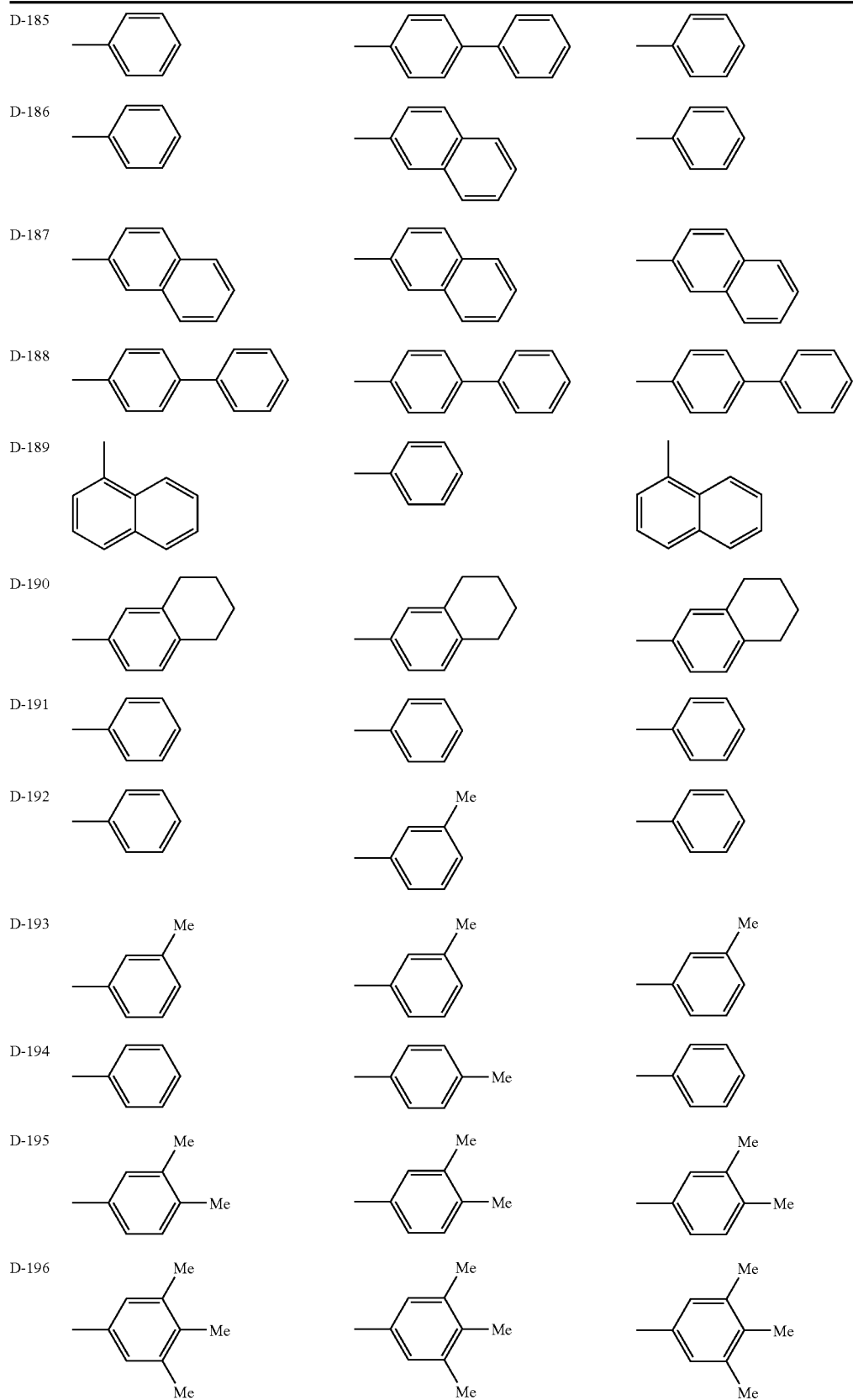

-continued
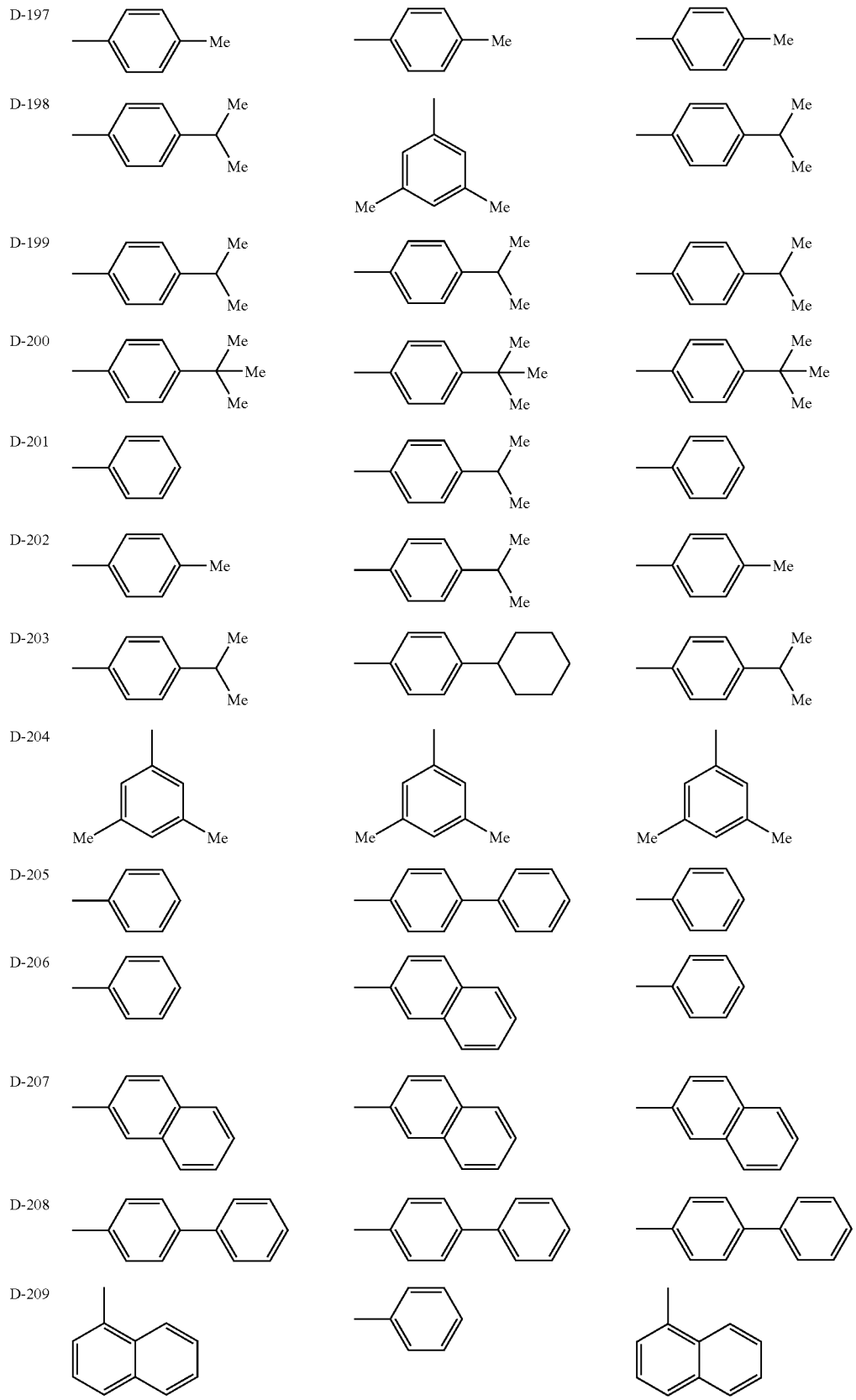

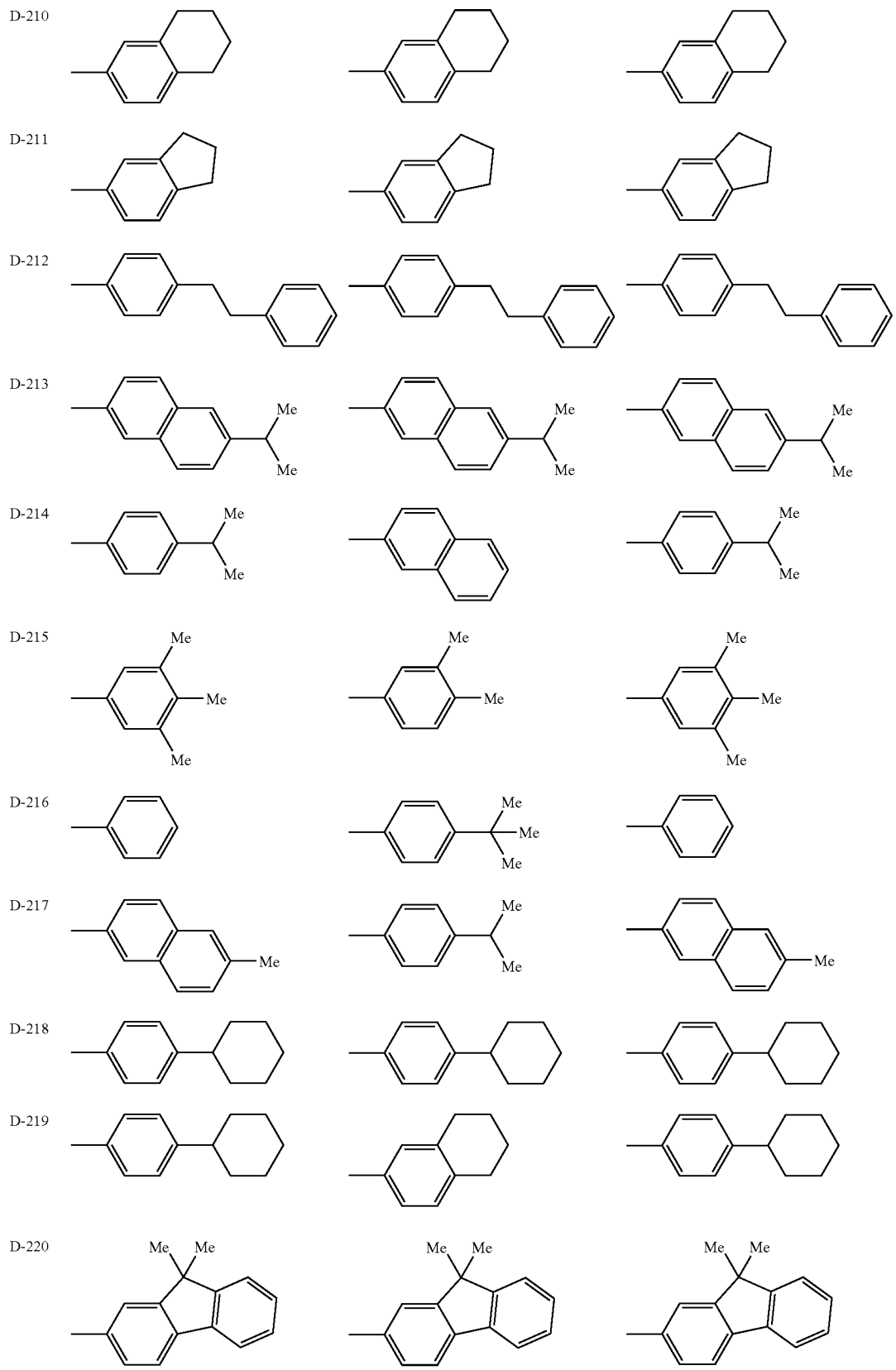

-continued
| | | | |
|---|---|---|---|
| D-221 | 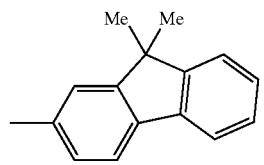 | 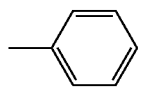 | 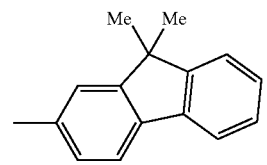 |
| D-222 | 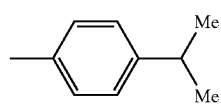 | 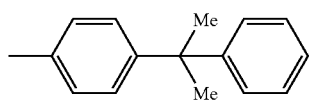 | 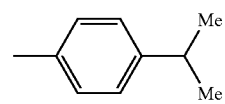 |
| D-223 | 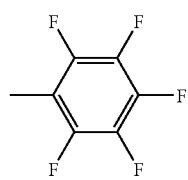 | 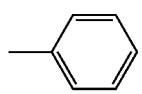 | 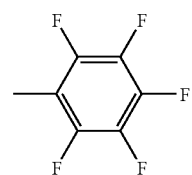 |
| D-224 | 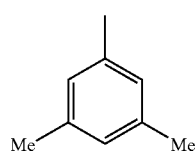 | 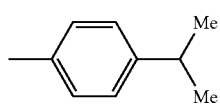 | 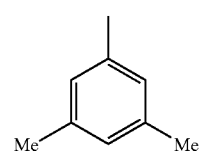 |
| D-225 | 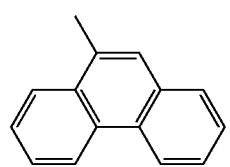 | 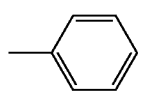 | 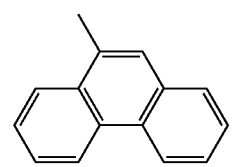 |
| D-226 | 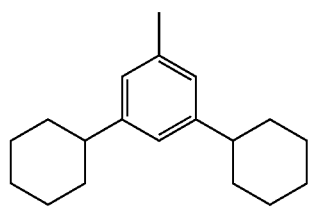 | 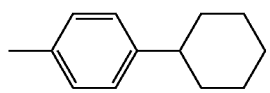 | 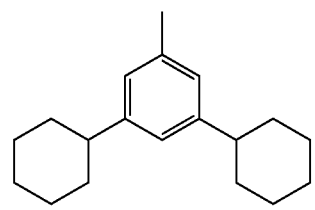 |
| D-227 | 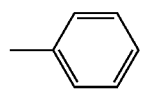 | 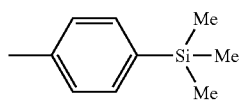 | 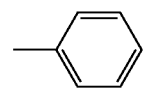 |
| D-228 | 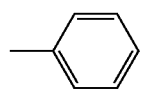 | 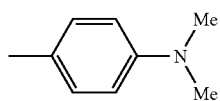 | 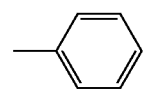 |
| D-229 | 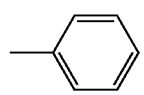 | 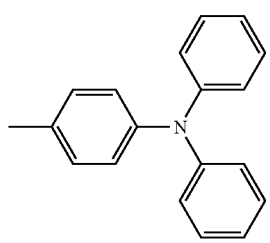 | 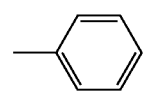 |
| D-230 | 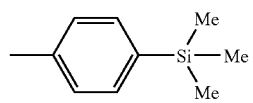 | 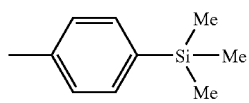 | 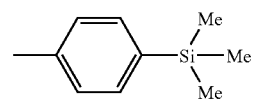 |

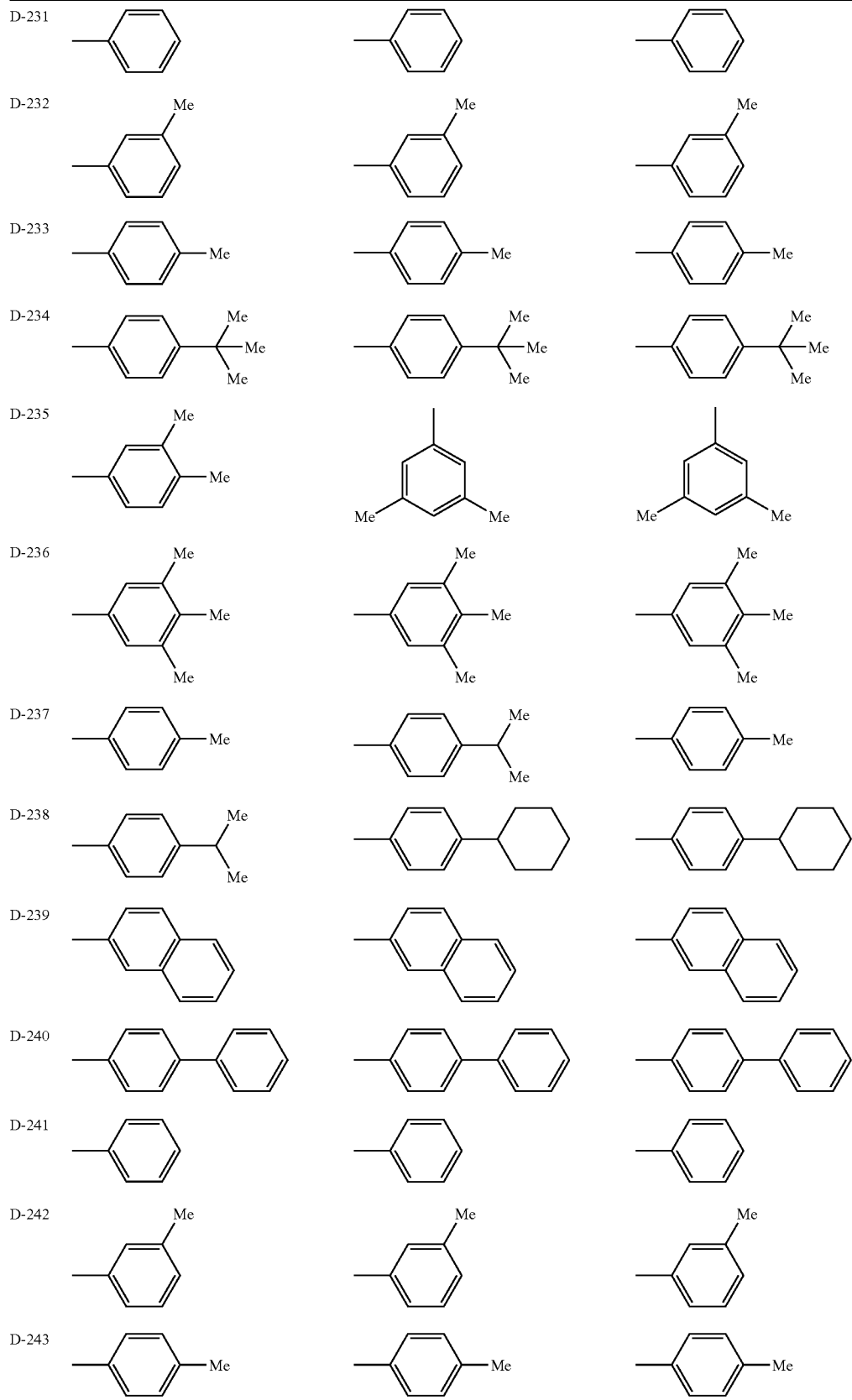

-continued
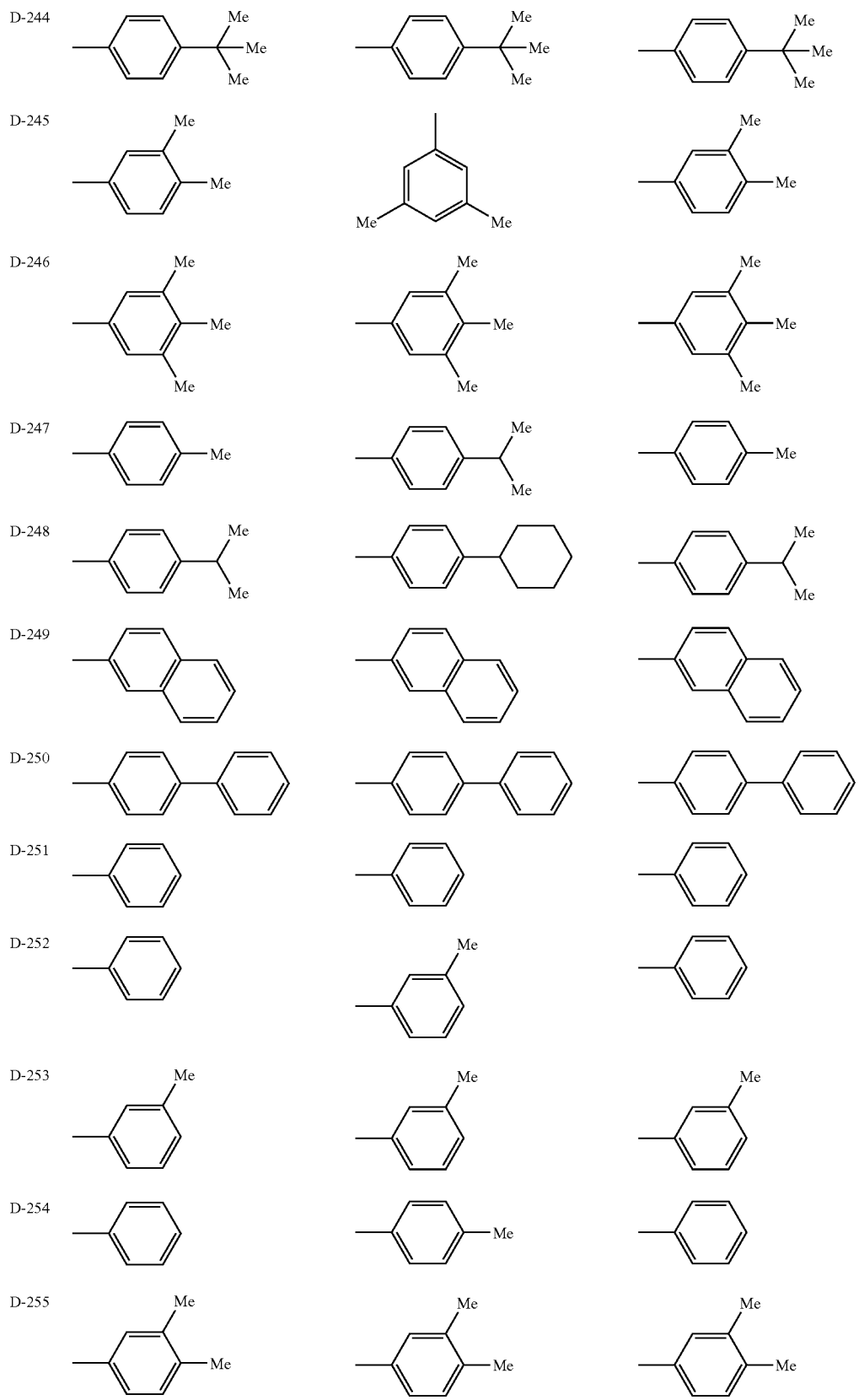

-continued
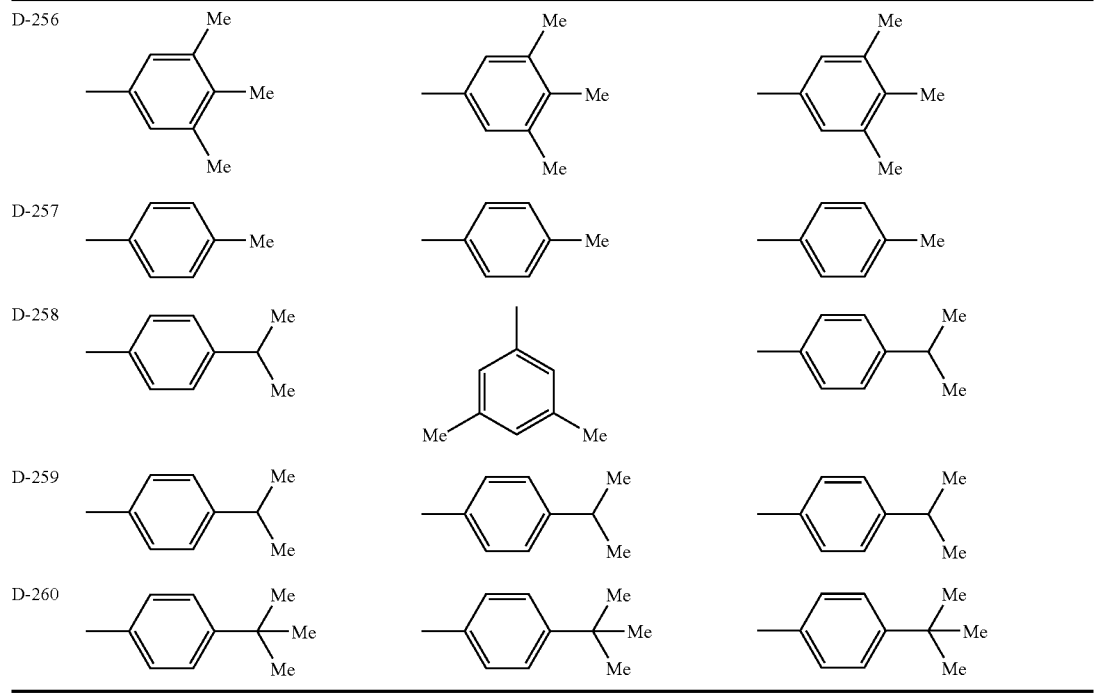
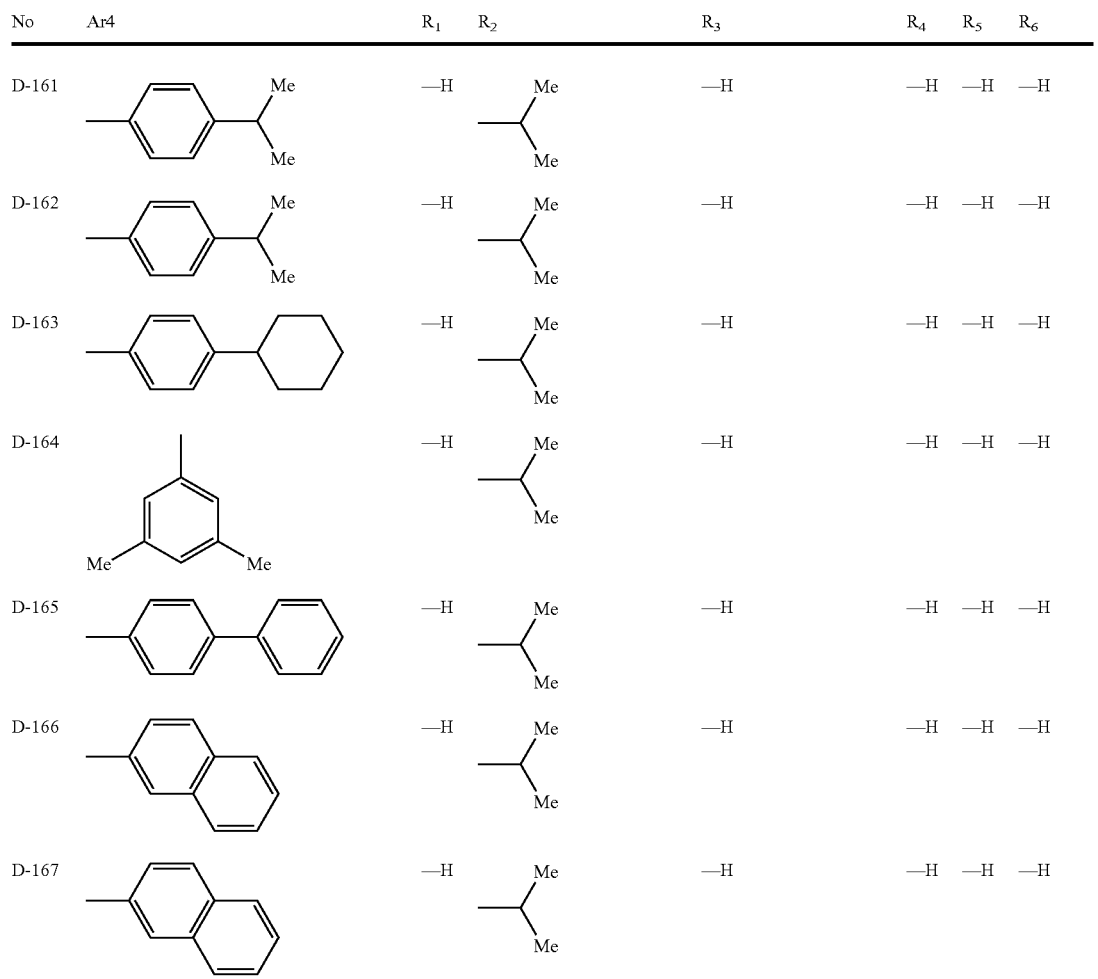

-continued
| | | | | | | |
|---|---|---|---|---|---|---|
| D-168 | 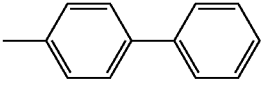 | —H |  Me / Me | —H | —H | —H —H |
| D-169 | 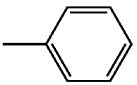 | —H | Me / Me | —H | —H | —H —H |
| D-170 |  | —H | Me / Me | —H | —H | —H —H |
| D-171 | 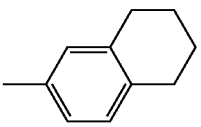 | —H —H | |  Me / Me | —H | —H —H |
| D-172 | 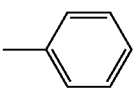 Me | —H —H | | Me / Me | —H | —H —H |
| D-173 |  Me | —H —H | | Me / Me | —H | —H —H |
| D-174 | 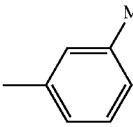 Me | —H —H | | Me / Me | —H | —H —H |
| D-175 |  Me Me | —H —H | | Me / Me | —H | —H —H |
| D-176 | 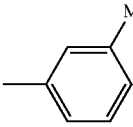 Me Me Me | —H —H | | Me / Me | —H | —H —H |
| D-177 |  Me | —H —H | | Me / Me | —H | —H —H |
| D-178 |  Me Me | —H —H | | Me / Me | —H | —H —H |
| D-179 |  Me / Me | —H —H | | Me / Me | —H | —H —H |

-continued

| | | | | | | | |
|---|---|---|---|---|---|---|---|
| D-180 | 4-cumyl-phenyl (C(Me)₂Me) | —H | —H | isopropyl (CH(Me)Me) | —H | —H | —H |
| D-181 | 4-isopropyl-phenyl (CH(Me)Me) | —H | —H | isopropyl | —H | —H | —H |
| D-182 | 4-(1-methylethyl)phenyl | —H | —H | isopropyl | —H | —H | —H |
| D-183 | 4-cyclohexyl-phenyl | —H | —H | isopropyl | —H | —H | —H |
| D-184 | 3,5-dimethyl-phenyl | —H | —H | isopropyl | —H | —H | —H |
| D-185 | 4-biphenyl | —H | —H | isopropyl | —H | —H | —H |
| D-186 | 2-naphthyl | —H | —H | isopropyl | —H | —H | —H |
| D-187 | 2-naphthyl | —H | —H | isopropyl | —H | —H | —H |
| D-188 | 4-biphenyl | —H | —H | isopropyl | —H | —H | —H |
| D-189 | phenyl | —H | —H | isopropyl | —H | —H | —H |
| D-190 | 5,6,7,8-tetrahydro-2-naphthyl | —H | —H | isopropyl | —H | —H | —H |
| D-191 | phenyl | —H | tert-butyl (C(Me)₃) | —H | —H | —H | —H |
| D-192 | 3-methyl-phenyl | —H | tert-butyl | —H | —H | —H | —H |

-continued

| | | | | | | | |
|---|---|---|---|---|---|---|---|
| D-193 | 3-methylphenyl (m-tolyl with Me) | —H | —C(Me)₃ | —H | —H | —H | —H |
| D-194 | 4-methylphenyl | —H | —C(Me)₃ | —H | —H | —H | —H |
| D-195 | 2,4-dimethylphenyl | —H | —C(Me)₃ | —H | —H | —H | —H |
| D-196 | 2,4,6-trimethylphenyl | —H | —C(Me)₃ | —H | —H | —H | —H |
| D-197 | 4-methylphenyl | —H | —C(Me)₃ | —H | —H | —H | —H |
| D-198 | 3,5-dimethylphenyl | —H | —C(Me)₃ | —H | —H | —H | —H |
| D-199 | 4-isopropylphenyl | —H | —C(Me)₃ | —H | —H | —H | —H |
| D-200 | 4-tert-butylphenyl | —H | —C(Me)₃ | —H | —H | —H | —H |
| D-201 | 4-isopropylphenyl | —H | cyclohexyl | —H | —H | —H | —H |
| D-202 | 4-isopropylphenyl | —H | cyclohexyl | —H | —H | —H | —H |
| D-203 | 4-cyclohexylphenyl | —H | cyclohexyl | —H | —H | —H | —H |
| D-204 | 3,5-dimethylphenyl | —H | cyclohexyl | —H | —H | —H | —H |

-continued

| | | | | | | | |
|---|---|---|---|---|---|---|---|
| D-205 | 4-phenylphenyl | —H | —H | cyclohexyl | —H | —H | —H |
| D-206 | 2-naphthyl | —H | —H | cyclohexyl | —H | —H | —H |
| D-207 | 2-naphthyl | —H | —H | cyclohexyl | —H | —H | —H |
| D-208 | 4-phenylphenyl | —H | —H | cyclohexyl | —H | —H | —H |
| D-209 | phenyl | —H | —Me | —Me | —H | —H | —H |
| D-210 | 5,6,7,8-tetrahydronaphth-2-yl | —H | —Me | —Me | —H | —H | —H |
| D-211 | 2,3-dihydro-1H-inden-5-yl | —H | —OMe | —H | —H | —H | —H |
| D-212 | 4-(2-phenylethyl)phenyl | —H | —OMe | —H | —H | —H | —H |
| D-213 | 6-isopropylnaphth-2-yl | —H | —OMe | —H | —H | —H | —H |
| D-214 | 2-naphthyl | —H | 2-methoxyphenyl | —H | —H | —H | —H |
| D-215 | 2,4-dimethylphenyl | —H | 2-methoxyphenyl | —H | —H | —H | —H |
| D-216 | 4-tert-butylphenyl | —H | 2-methoxyphenyl | —H | —H | —H | —H |
| D-217 | 4-isopropylphenyl | —H | —H | —OMe | —H | —H | —H |

-continued
| | | | | | | |
|---|---|---|---|---|---|---|
| D-218 | 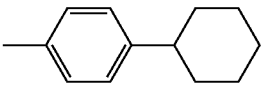 | —H | —H | —OMe | —H | —H —H |
| D-219 | 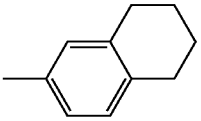 | —H | —H | —H | —H | —H —H |
| D-220 | 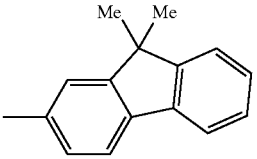 | —H | —H | —H | —H | —H —H |
| D-221 | 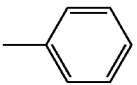 | —H | 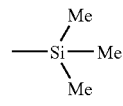 | —H | —H | —H —H |
| D-222 | 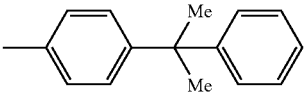 | —H | 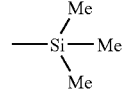 | —H | —H | —H —H |
| D-223 | 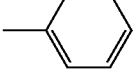 | —H | 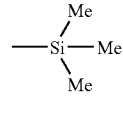 | —H | —H | —H —H |
| D-224 | 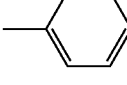 | —H | 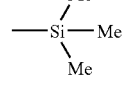 | —H | —H | —H —H |
| D-225 | 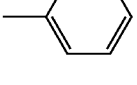 | —H | 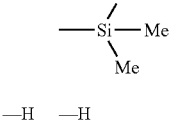 | —H | —H | —H —H |
| D-226 | 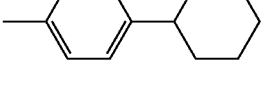 | —H | —H | 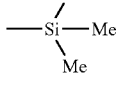 | —H | —H —H |
| D-227 | 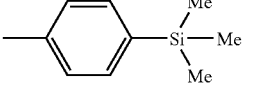 | —H | —H | 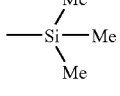 | —H | —H —H |
| D-228 | 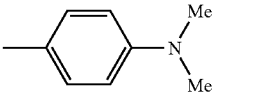 | —H | —H | 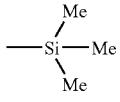 | —H | —H —H |
| D-229 | 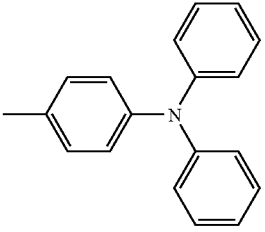 | —H | —H | 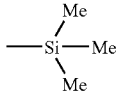 | —H | —H —H |

-continued
| | | | | | | | |
|---|---|---|---|---|---|---|---|
| D-230 | 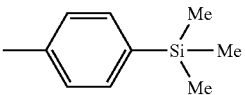 | —H | —Me | 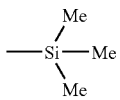 | —H | —H | —H |
| D-231 | 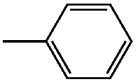 | —H | —H | 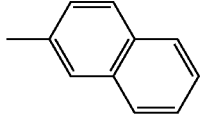 | —H | —H | —H |
| D-232 | 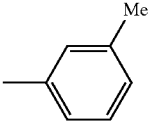 | —H | —H | 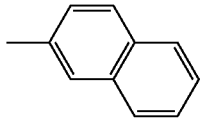 | —H | —H | —H |
| D-233 | 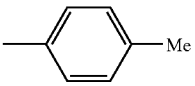 | —H | —H | 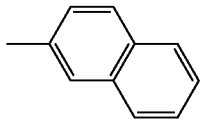 | —H | —H | —H |
| D-234 | 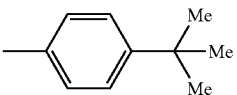 | —H | —H | 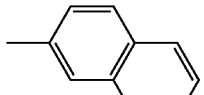 | —H | —H | —H |
| D-235 | 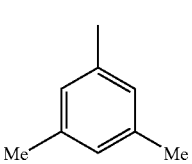 | —H | —H | 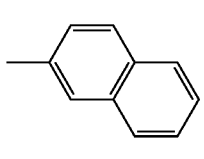 | —H | —H | —H |
| D-236 | 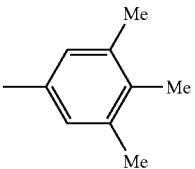 | —H | —H | 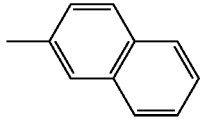 | —H | —H | —H |
| D-237 | 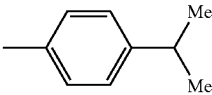 | —H | —H | 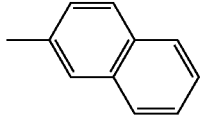 | —H | —H | —H |
| D-238 | 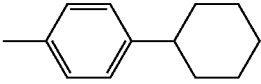 | —H | —H | 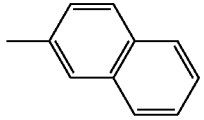 | —H | —H | —H |
| D-239 | 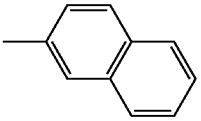 | —H | —H | 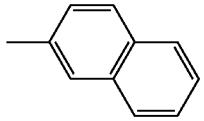 | —H | —H | —H |
| D-240 | 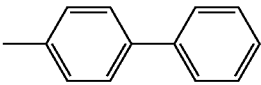 | —H | —H | 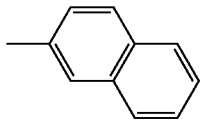 | —H | —H | —H |

-continued
| | | | | | | | |
|---|---|---|---|---|---|---|---|
| D-241 | 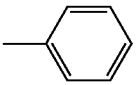 | —H | 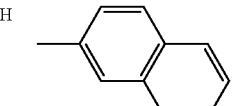 | —H | —H | —H | —H |
| D-242 | 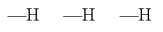 | —H | 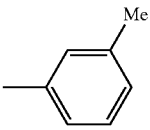 | —H | —H | —H | —H |
| D-243 | 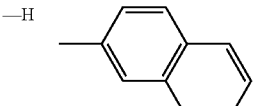 | —H | 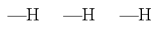 | —H | —H | —H | —H |
| D-244 | 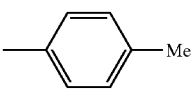 | —H | 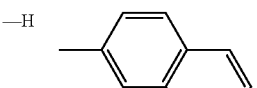 | —H | —H | —H | —H |
| D-245 | 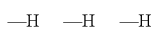 | —H | 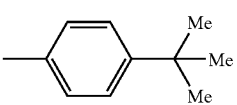 | —H | —H | —H | —H |
| D-246 | 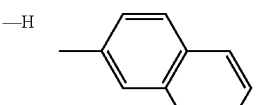 | —H | 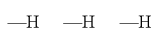 | —H | —H | —H | —H |
| D-247 | 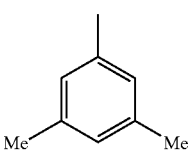 | —H | 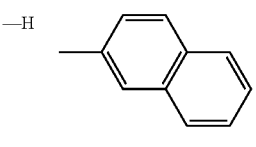 | —H | —H | —H | —H |
| D-248 | 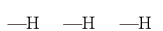 | —H | 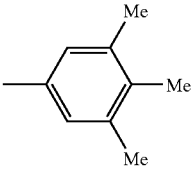 | —H | —H | —H | —H |
| D-249 | 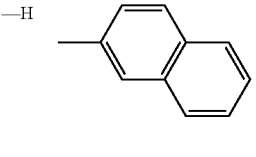 | —H | 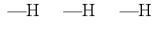 | —H | —H | —H | —H |
| D-250 | 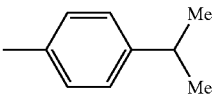 | —H | 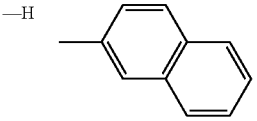 | —H | —H | —H | —H |
| D-251 | 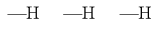 | —H | 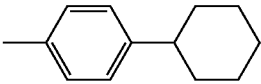 | —H | —H | —H | —H |

-continued

| No | R | | | | | |
|---|---|---|---|---|---|---|
| D-252 | 1,3-dimethylphenyl | —H | phenyl | —H | —H —H —H |
| D-253 | 1,3-dimethylphenyl | —H | phenyl | —H | —H —H —H |
| D-254 | 4-methylphenyl | —H | phenyl | —H | —H —H —H |
| D-255 | 3,4-dimethylphenyl | —H | phenyl | —H | —H —H —H |
| D-256 | 3,4,5-trimethylphenyl | —H | phenyl | —H | —H —H —H |
| D-257 | 4-methylphenyl | —H | phenyl | —H | —H —H —H |
| D-258 | 3,5-dimethylphenyl | —H | phenyl | —H | —H —H —H |
| D-259 | 4-isopropylphenyl | —H | phenyl | —H | —H —H —H |
| D-260 | 4-tert-butylphenyl (CMe₃) | —H | phenyl | —H | —H —H —H |

| No | $R_7$ | $R_8$ | $R_9$ | $R_{10}$ |
|---|---|---|---|---|
| D-161 | isopropyl | —H | —H | —H |
| D-162 | isopropyl | —H | —H | —H |
| D-163 | isopropyl | —H | —H | —H |

-continued

| | | | | |
|---|---|---|---|---|
| D-164 | iPr (Me/Me) | —H | —H | —H |
| D-165 | iPr (Me/Me) | —H | —H | —H |
| D-166 | iPr (Me/Me) | —H | —H | —H |
| D-167 | iPr (Me/Me) | —H | —H | —H |
| D-168 | iPr (Me/Me) | —H | —H | —H |
| D-169 | iPr (Me/Me) | —H | —H | —H |
| D-170 | iPr (Me/Me) | —H | —H | —H |
| D-171 | —H | iPr (Me/Me) | —H | —H |
| D-172 | —H | iPr (Me/Me) | —H | —H |
| D-173 | —H | iPr (Me/Me) | —H | —H |
| D-174 | —H | iPr (Me/Me) | —H | —H |
| D-175 | —H | iPr (Me/Me) | —H | —H |
| D-176 | —H | iPr (Me/Me) | —H | —H |
| D-177 | —H | iPr (Me/Me) | —H | —H |

-continued

| | | | | |
|---|---|---|---|---|
| D-178 | —H | iPr (Me, Me) | —H | —H |
| D-179 | —H | iPr (Me, Me) | —H | —H |
| D-180 | —H | iPr (Me, Me) | —H | —H |
| D-181 | —H | iPr (Me, Me) | —H | —H |
| D-182 | —H | iPr (Me, Me) | —H | —H |
| D-183 | —H | iPr (Me, Me) | —H | —H |
| D-184 | —H | iPr (Me, Me) | —H | —H |
| D-185 | —H | iPr (Me, Me) | —H | —H |
| D-186 | —H | iPr (Me, Me) | —H | —H |
| D-187 | —H | iPr (Me, Me) | —H | —H |
| D-188 | —H | iPr (Me, Me) | —H | —H |
| D-189 | —H | iPr (Me, Me) | —H | —H |
| D-190 | —H | iPr (Me, Me) | —H | —H |
| D-191 | tBu (Me, Me, Me) | —H | —H | —H |

-continued

| | | | | |
|---|---|---|---|---|
| D-192 | tBu (Me, Me, Me) | —H | —H | —H |
| D-193 | tBu | —H | —H | —H |
| D-194 | tBu | —H | —H | —H |
| D-195 | tBu | —H | —H | —H |
| D-196 | tBu | —H | —H | —H |
| D-197 | tBu | —H | —H | —H |
| D-198 | tBu | —H | —H | —H |
| D-199 | tBu | —H | —H | —H |
| D-200 | tBu | —H | —H | —H |
| D-201 | cyclohexyl | —H | —H | —H |
| D-202 | cyclohexyl | —H | —H | —H |
| D-203 | cyclohexyl | —H | —H | —H |
| D-204 | cyclohexyl | —H | —H | —H |
| D-205 | —H | | cyclohexyl | —H —H |
| D-206 | —H | | cyclohexyl | —H —H |

-continued

| | | | | |
|---|---|---|---|---|
| D-207 | —H | cyclohexyl | —H | —H |
| D-208 | —H | cyclohexyl | —H | —H |
| D-209 | —Me | —Me | —H | —H |
| D-210 | —Me | —Me | —H | —H |
| D-211 | —OMe | —H | —H | —H |
| D-212 | —OMe | —H | —H | —H |
| D-213 | —OMe | —H | —H | —H |
| D-214 | PhOMe | —H | —H | —H |
| D-215 | PhOMe | —H | —H | —H |
| D-216 | PhOMe | —H | —H | —H |
| D-217 | —H | —OMe | —H | —H |
| D-218 | —H | —OMe | —H | —H |
| D-219 | —H | PhOMe | —H | —H |
| D-220 | —H | PhOMe | —H | —H |
| D-221 | —SiMe$_3$ | —H | —H | —H |
| D-222 | —SiMe$_3$ | —H | —H | —H |
| D-223 | —SiMe$_3$ | —H | —H | —H |
| D-224 | —SiMe$_3$ | —H | —H | —H |
| D-225 | —SiMe$_3$ | —H | —H | —H |
| D-226 | —H | —SiMe$_3$ | —H | —H |

-continued

| | | | | |
|---|---|---|---|---|
| D-227 | —H | —Si(Me)(Me)Me | —H | —H |
| D-228 | —H | —Si(Me)(Me)Me | —H | —H |
| D-229 | —H | —Si(Me)(Me)Me | —H | —H |
| D-230 | —H | —Si(Me)(Me)Me | —H | —H |
| D-231 | —H | 2-naphthyl | —H | —H |
| D-232 | —H | 2-naphthyl | —H | —H |
| D-233 | —H | 2-naphthyl | —H | —H |
| D-234 | —H | 2-naphthyl | —H | —H |
| D-235 | —H | 2-naphthyl | —H | —H |
| D-236 | —H | 2-naphthyl | —H | —H |
| D-237 | —H | 2-naphthyl | —H | —H |
| D-238 | —H | 2-naphthyl | —H | —H |

-continued
| | | | | |
|---|---|---|---|---|
| D-239 | —H | 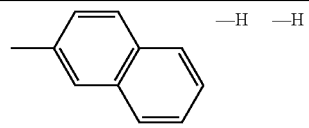 | —H | —H |
| D-240 | —H | 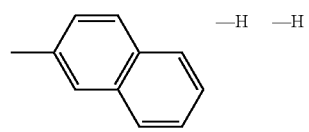 | —H | —H |
| D-241 | 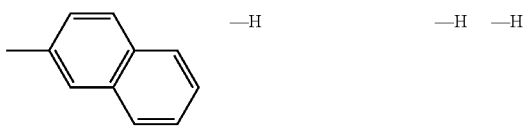 | —H | —H | —H |
| D-242 |  | —H | —H | —H |
| D-243 | 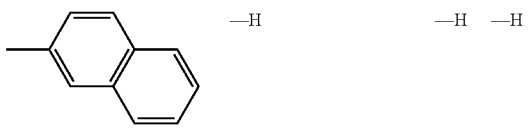 | —H | —H | —H |
| D-244 |  | —H | —H | —H |
| D-245 | 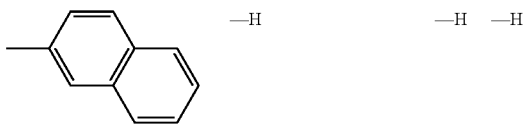 | —H | —H | —H |
| D-246 |  | —H | —H | —H |
| D-247 |  | —H | —H | —H |
| D-248 |  | —H | —H | —H |
| D-249 |  | —H | —H | —H |
| D-250 | 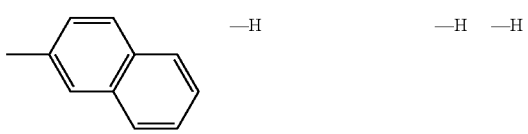 | —H | —H | —H |

-continued

| | No | | Ar2 or structure | Col3 | Col4 | Col5 |
|---|---|---|---|---|---|---|
| | D-251 | | phenyl | —H | —H | —H |
| | D-252 | | phenyl | —H | —H | —H |
| | D-253 | | phenyl | —H | —H | —H |
| | D-254 | | phenyl | —H | —H | —H |
| | D-255 | | phenyl | —H | —H | —H |
| | D-256 | | phenyl | —H | —H | —H |
| | D-257 | | phenyl | —H | —H | —H |
| | D-258 | | phenyl | —H | —H | —H |
| | D-259 | | phenyl | —H | —H | —H |
| | D-260 | | phenyl | —H | —H | —H |

| No | Ar1 | Ar2 | Ar3 | Ar4 |
|---|---|---|---|---|
| D-261 | phenyl | 4-isopropylphenyl | phenyl | 4-isopropylphenyl |
| D-262 | 4-methylphenyl | 4-isopropylphenyl | 4-methylphenyl | 4-(1-methylethyl)phenyl |
| D-263 | 4-isopropylphenyl | 4-cyclohexylphenyl | 4-isopropylphenyl | 4-cyclohexylphenyl |

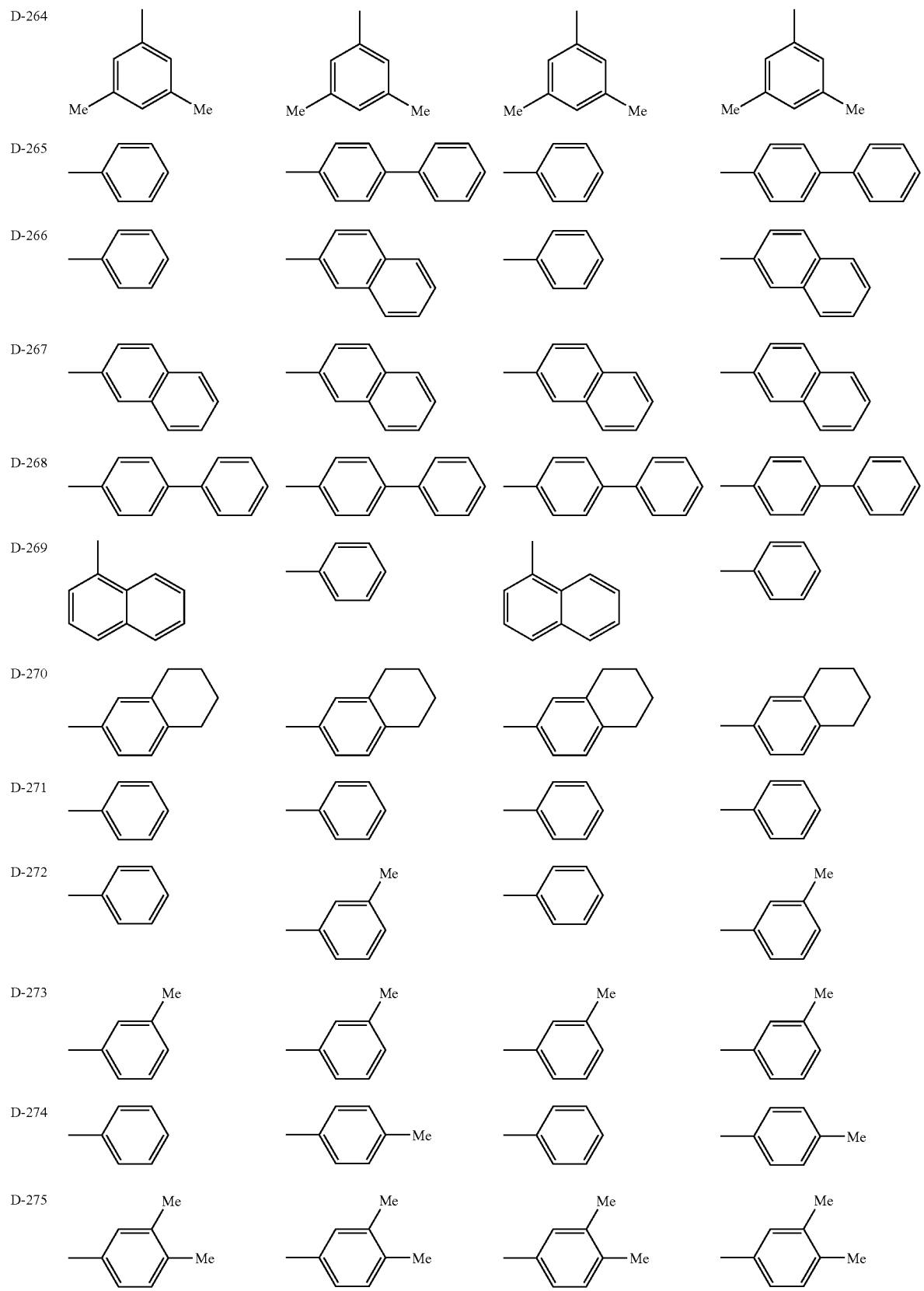

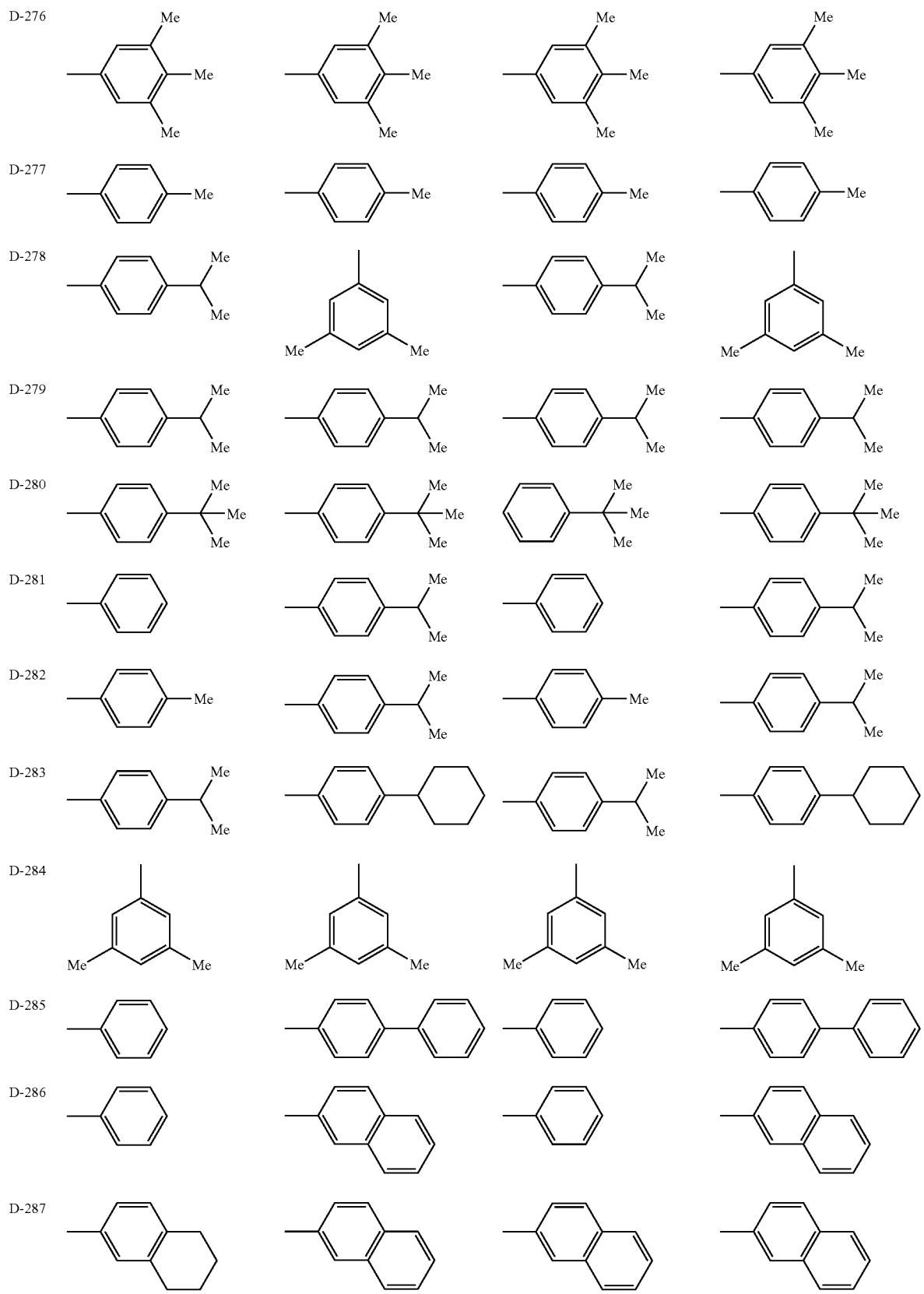

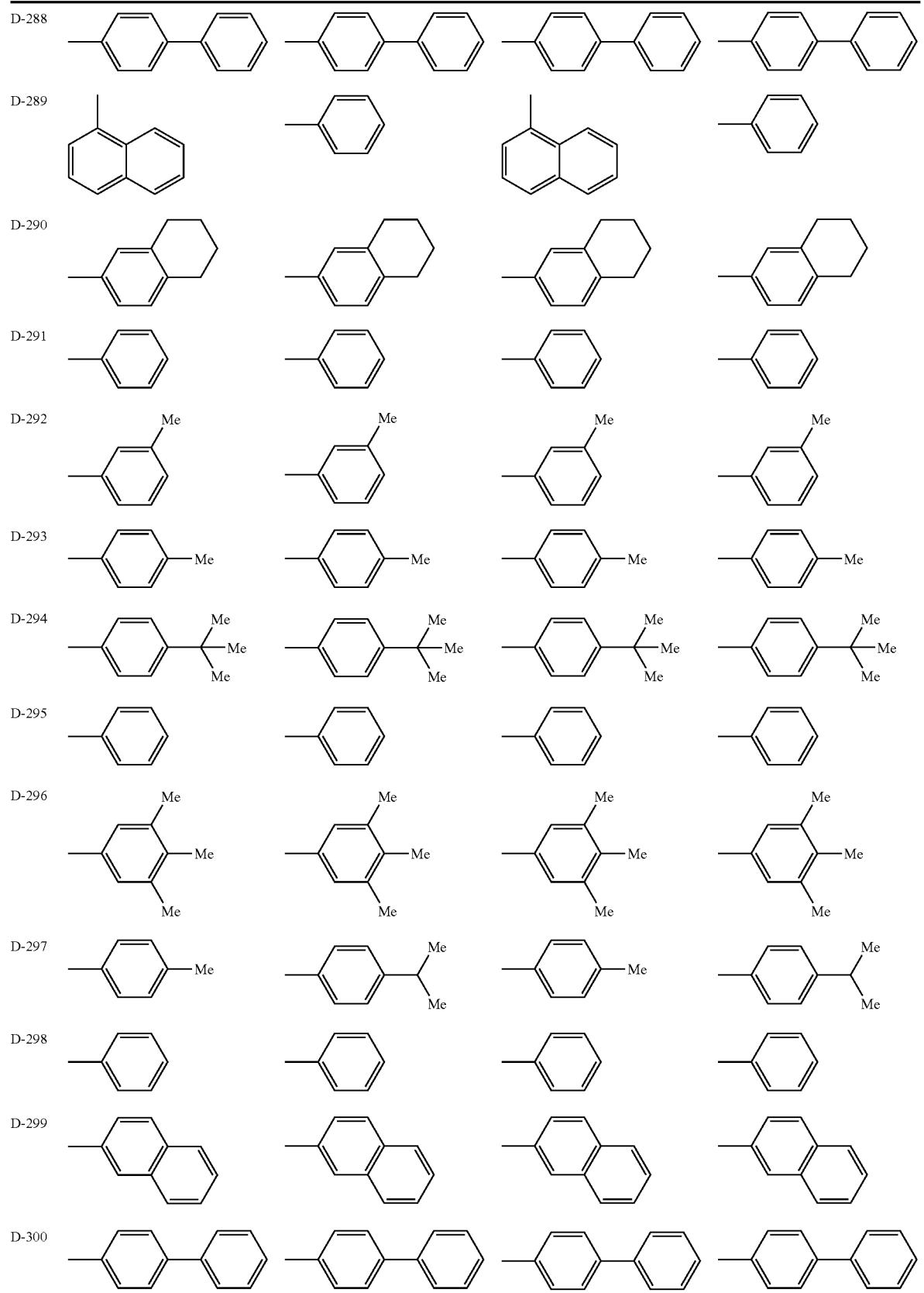

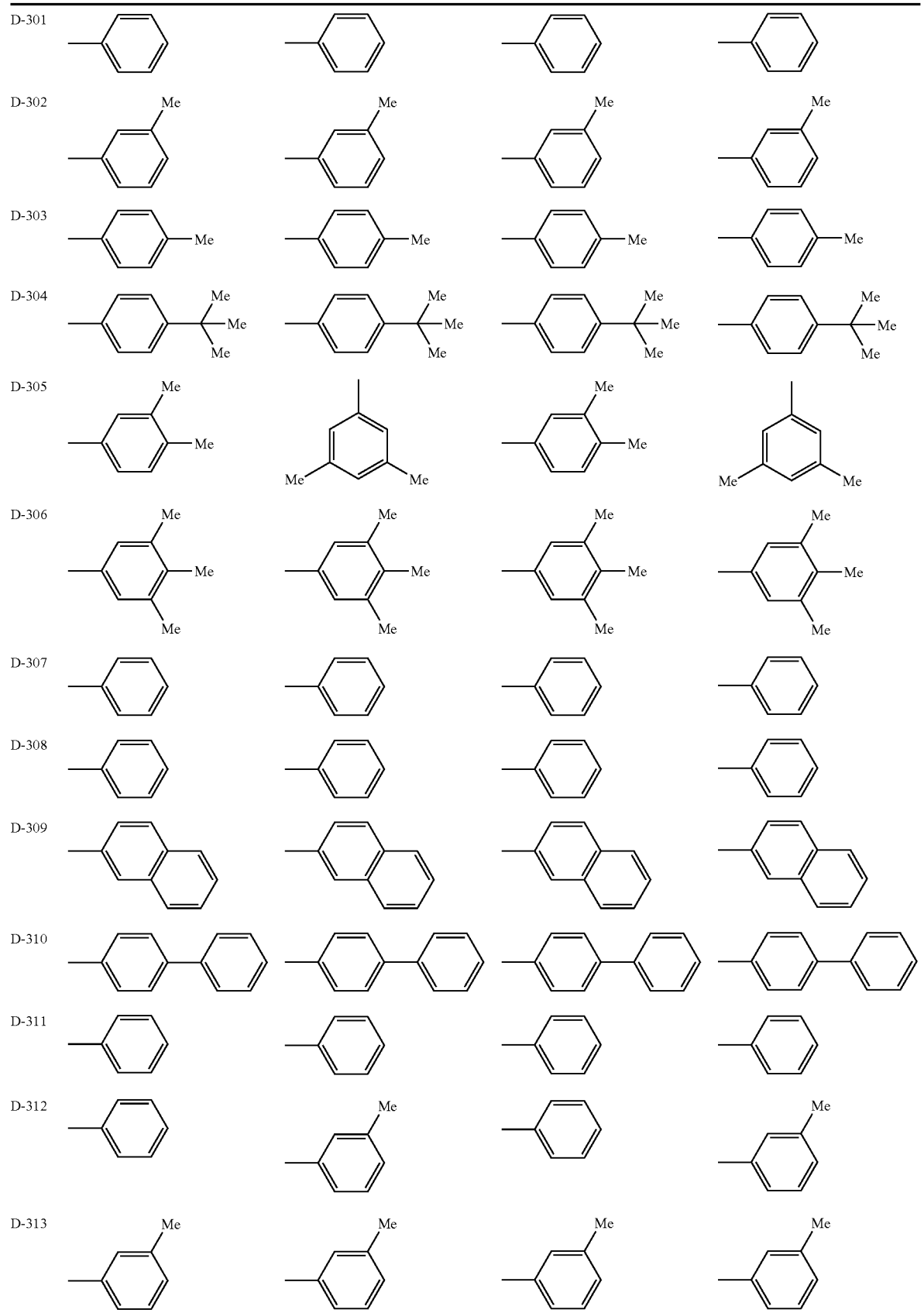

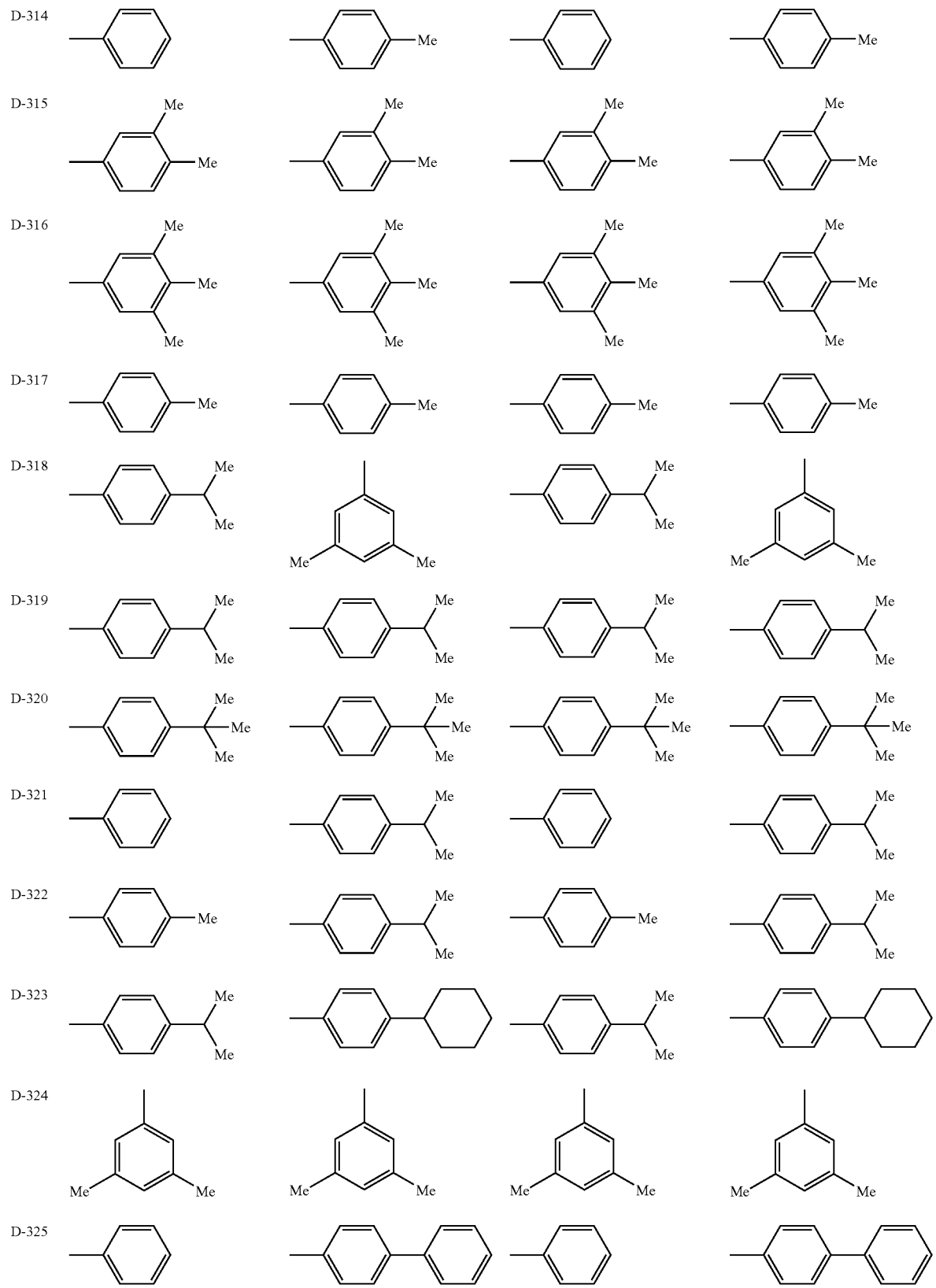

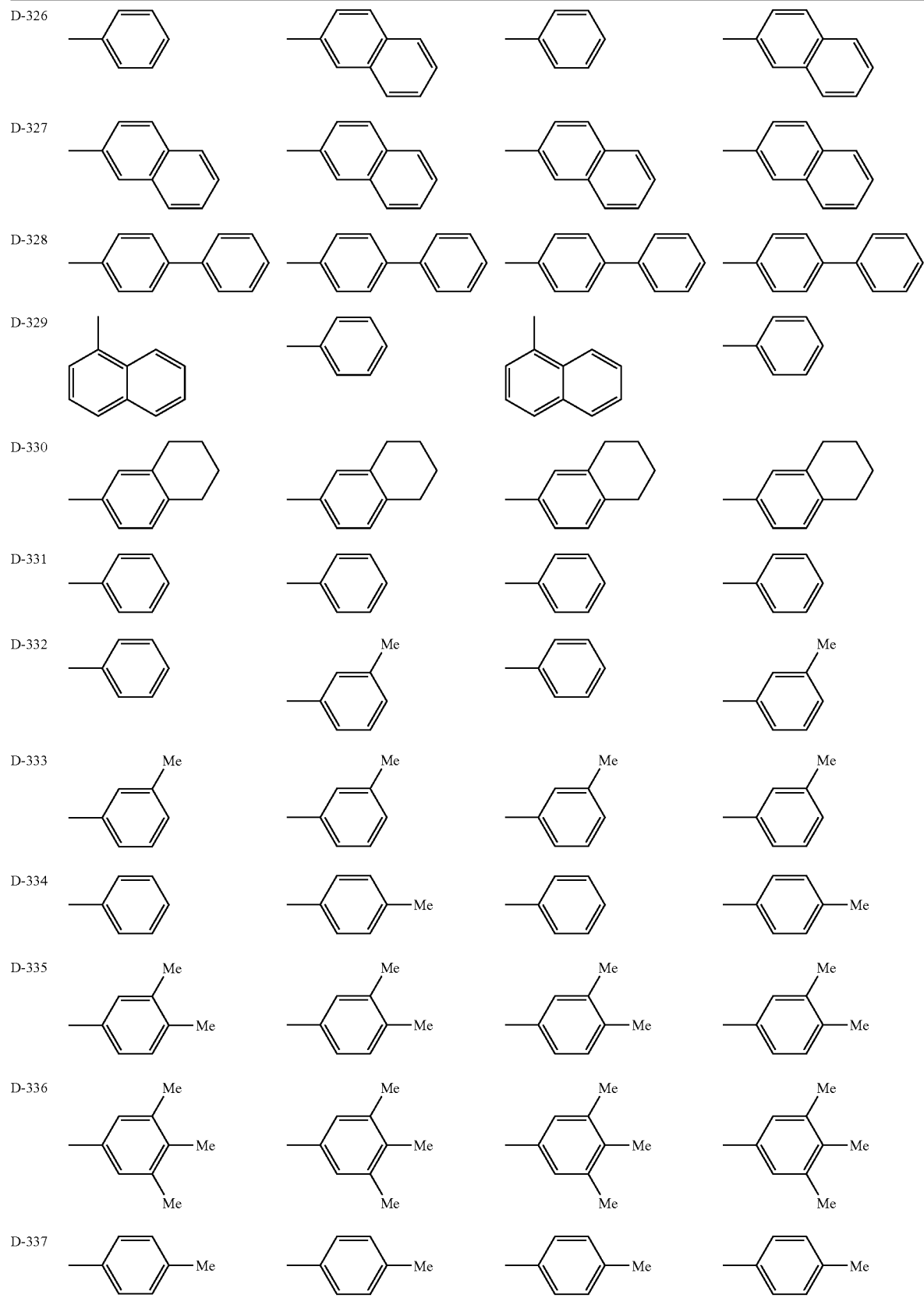

-continued
| No | | | | | | | |
|---|---|---|---|---|---|---|---|
| D-338 | 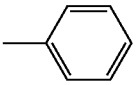 | | 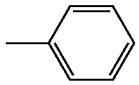 | | 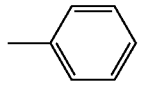 | | 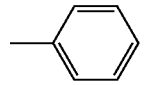 |
| D-339 | 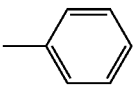 | | 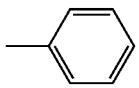 | | 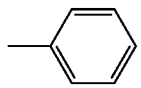 | | 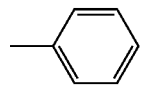 |
| D-340 | 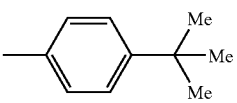 | | 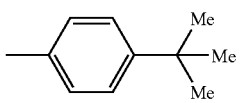 | | 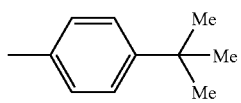 | | 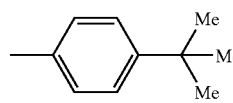 |
| No | $R_1$ | $R_2$ | $R_3$ | $R_4$ | $R_5$ | $R_6$ | $R_7$ |
|---|---|---|---|---|---|---|---|
| D-261 | —H | 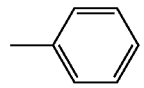 | —H | —H | —H | —H | 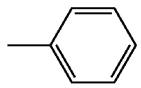 |
| D-262 | —H | 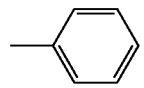 | —H | —H | —H | —H | 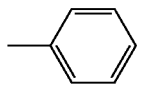 |
| D-263 | —H | 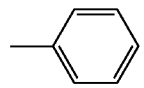 | —H | —H | —H | —H | 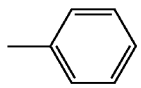 |
| D-264 | —H | 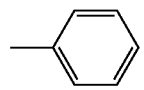 | —H | —H | —H | —H | 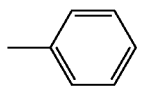 |
| D-265 | —H | 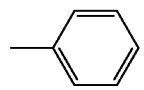 | —H | —H | —H | —H | 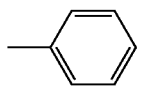 |
| D-266 | —H | 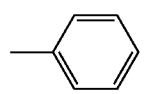 | —H | —H | —H | —H | 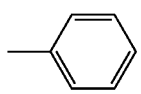 |
| D-267 | —H | 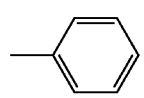 | —H | —H | —H | —H | 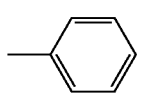 |
| D-268 | —H | 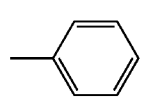 | —H | —H | —H | —H | 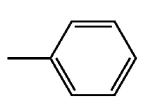 |
| D-269 | —H | 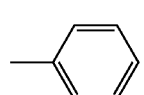 | —H | —H | —H | —H | 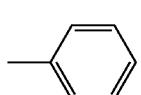 |
| D-270 | —H | 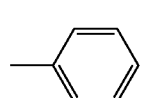 | —H | —H | —H | —H | 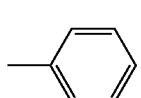 |
| D-271 | —H | —H | 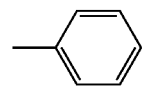 | —H | —H | —H | —H |
| D-272 | —H | —H | 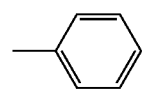 | —H | —H | —H | —H |

-continued
| | | | | | | | |
|---|---|---|---|---|---|---|---|
| D-273 | —H | —H | 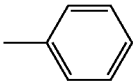 | —H | —H | —H | —H |
| D-274 | —H | —H | 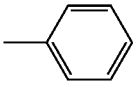 | —H | —H | —H | —H |
| D-275 | —H | —H | 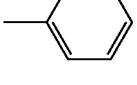 | —H | —H | —H | —H |
| D-276 | —H | —H | 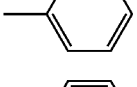 | —H | —H | —H | —H |
| D-277 | —H | —H | 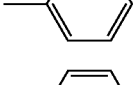 | —H | —H | —H | —H |
| D-278 | —H | —H | 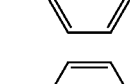 | —H | —H | —H | —H |
| D-279 | —H | —H | 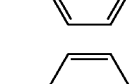 | —H | —H | —H | —H |
| D-280 | —H | —H | 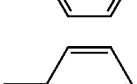 | —H | —H | —H | —H |
| D-281 | —H | —H | 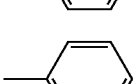 | —H | —H | —H | —H |
| D-282 | —H | —H | 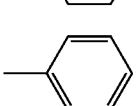 | —H | —H | —H | —H |
| D-283 | —H | —H | 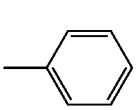 | —H | —H | —H | —H |
| D-284 | —H | —H | 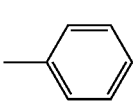 | —H | —H | —H | —H |
| D-285 | —H | —H | 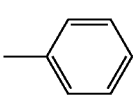 | —H | —H | —H | —H |
| D-286 | —H | —H | 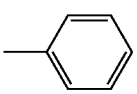 | —H | —H | —H | —H |
| D-287 | —H | —H | 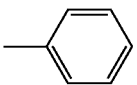 | —H | —H | —H | —H |
| D-288 | —H | —H |  | —H | —H | —H | —H |

-continued
| | | | | | | | |
|---|---|---|---|---|---|---|---|
| D-289 | —H | —H | 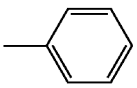 | —H | —H | —H | —H |
| D-290 | —H | —H | 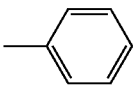 | —H | —H | —H | —H |
| D-291 | —H | —H | 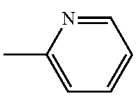 | —H | —H | —H | —H |
| D-292 | —H | —H | 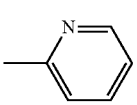 | —H | —H | —H | —H |
| D-293 | —H | —H | 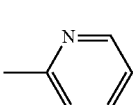 | —H | —H | —H | —H |
| D-294 | —H | —H | 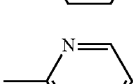 | —H | —H | —H | —H |
| D-295 | —H | —H | 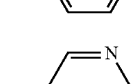 | —H | —H | —H | —H |
| D-296 | —H | —H | 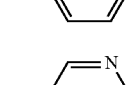 | —H | —H | —H | —H |
| D-297 | —H | —H | 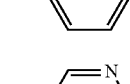 | —H | —H | —H | —H |
| D-298 | —H | —H | 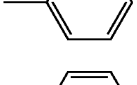 | —H | —H | —H | —H |
| D-299 | —H | —H | 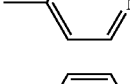 | —H | —H | —H | —H |
| D-300 | —H | —H | 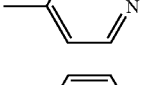 | —H | —H | —H | —H |
| D-301 | —H | 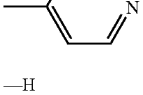 | —H | —H | —H | —H | 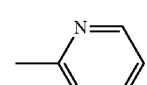 |
| D-302 | —H | 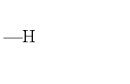 | —H | —H | —H | —H | 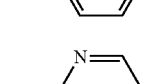 |
| D-303 | —H | 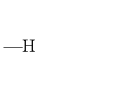 | —H | —H | —H | —H | 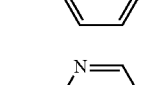 |

-continued

| | | | | | | | |
|---|---|---|---|---|---|---|---|
| D-304 | —H | 3-pyridyl | —H | —H | —H | —H | 3-pyridyl |
| D-305 | —H | 3-pyridyl | —H | —H | —H | —H | 3-pyridyl |
| D-306 | —H | 3-pyridyl | —H | —H | —H | —H | 3-pyridyl |
| D-307 | —H | 3-pyridyl | —H | —H | —H | —H | 3-pyridyl |
| D-308 | —H | 4-pyridyl | —H | —H | —H | —H | 4-pyridyl |
| D-309 | —H | 4-pyridyl | —H | —H | —H | —H | 4-pyridyl |
| D-310 | —H | 4-pyridyl | —H | —H | —H | —H | 4-pyridyl |
| D-311 | —H | NPh₂ | —H | —H | —H | —H | NPh₂ |
| D-312 | —H | NPh₂ | —H | —H | —H | —H | NPh₂ |
| D-313 | —H | NPh₂ | —H | —H | —H | —H | NPh₂ |
| D-314 | —H | NPh₂ | —H | —H | —H | —H | NPh₂ |
| D-315 | —H | NPh₂ | —H | —H | —H | —H | NPh₂ |
| D-316 | —H | NPh₂ | —H | —H | —H | —H | NPh₂ |
| D-317 | —H | NPh₂ | —H | —H | —H | —H | NPh₂ |
| D-319 | —H | NPh₂ | —H | —H | —H | —H | NPh₂ |

-continued
| | | | | | | | |
|---|---|---|---|---|---|---|---|
| D-320 | —H | 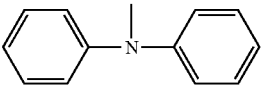 | —H | —H | —H | —H | 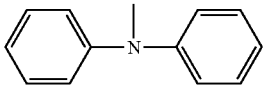 |
| D-321 | —H | 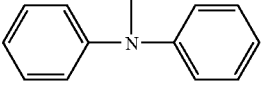 | —H | —H | —H | —H | 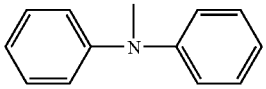 |
| D-322 | —H | 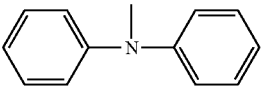 | —H | —H | —H | —H | 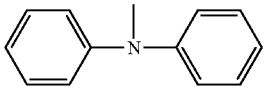 |
| D-323 | —H | 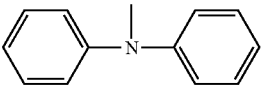 | —H | —H | —H | —H | 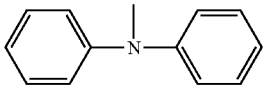 |
| D-324 | —H | 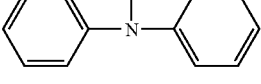 | —H | —H | —H | —H | 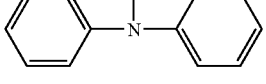 |
| D-325 | —H | 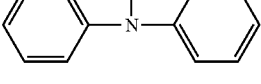 | —H | —H | —H | —H | 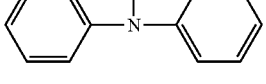 |
| D-326 | —H | 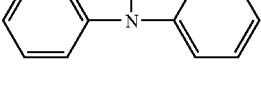 | —H | —H | —H | —H | 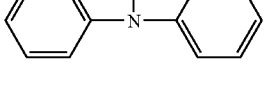 |
| D-327 | —H | 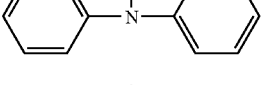 | —H | —H | —H | —H | 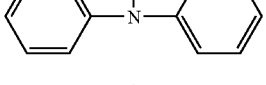 |
| D-328 | —H | 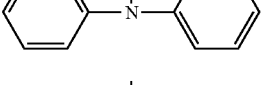 | —H | —H | —H | —H | 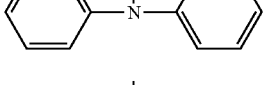 |
| D-329 | —H | 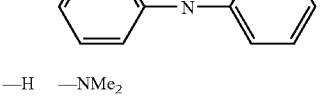 | —H | —H | —H | —H | 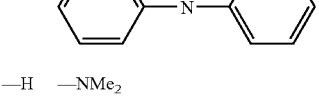 |
| D-330 | —H | —NMe$_2$ | | —H | —H | —H | —NMe$_2$ |
| D-331 | —H | —H | 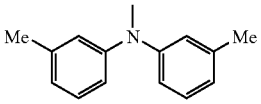 | —H | —H | —H | —H |
| D-332 | —H | —H | 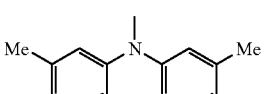 | —H | —H | —H | —H |
| D-333 | —H | —H | 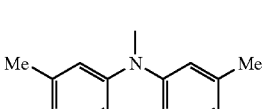 | —H | —H | —H | —H |
| D-334 | —H | —H |  | —H | —H | —H | —H |

-continued
| | | | | | | |
|---|---|---|---|---|---|---|
| D-335 | —H | —H | 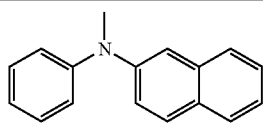 | —H —H | —H | —H |
| D-336 | —H | —H | 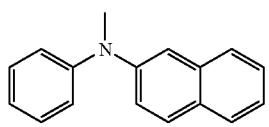 | —H —H | —H | —H |
| D-337 | —H | —H | 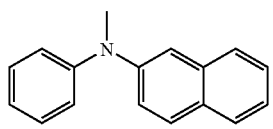 | —H —H | —H | —H |
| D-338 | —H | —H | 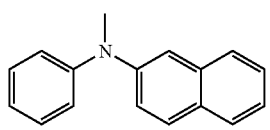 | —H —H | —H | —H |
| D-339 | —H | —H | —NMe$_2$ | —H —H | —H | —H |
| D-340 | —H | —H | —NMe$_2$ | —H —H | —H | —H |
| No | R$_8$ | R$_9$ | R$_{10}$ |
|---|---|---|---|
| D-261 | —H | —H | —H |
| D-262 | —H | —H | —H |
| D-263 | —H | —H | —H |
| D-264 | —H | —H | —H |
| D-265 | —H | —H | —H |
| D-266 | —H | —H | —H |
| D-267 | —H | —H | —H |
| D-268 | —H | —H | —H |
| D-269 | —H | —H | —H |
| D-270 | —H | —H | —H |
| D-271 | -Ph | —H | —H |
| D-272 | -Ph | —H | —H |
| D-273 | -Ph | —H | —H |
| D-274 | -Ph | —H | —H |
| D-275 | -Ph | —H | —H |
| D-276 | -Ph | —H | —H |
| D-277 | -Ph | —H | —H |

-continued

| | | | | |
|---|---|---|---|---|
| D-278 | phenyl | —H | —H | |
| D-279 | phenyl | —H | —H | |
| D-280 | pyridyl | —H | —H | |
| D-281 | pyridyl | —H | —H | |
| D-282 | pyridyl | —H | —H | |
| D-283 | phenyl | —H | —H | |
| D-284 | phenyl | —H | —H | |
| D-285 | phenyl | —H | —H | |
| D-286 | phenyl | —H | —H | |
| D-287 | phenyl | —H | —H | |
| D-288 | phenyl | —H | —H | |
| D-289 | phenyl | —H | —H | |
| D-290 | phenyl | —H | —H | |
| D-291 | pyridyl | —H | —H | |
| D-292 | pyridyl | —H | —H | |
| D-293 | pyridyl | —H | —H | |

-continued
| | | | | |
|---|---|---|---|---|
| D-294 | 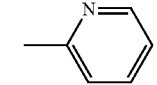 | —H | —H | |
| D-295 | 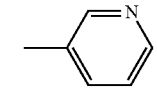 | —H | —H | |
| D-296 | 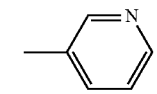 | —H | —H | |
| D-297 | 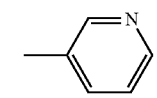 | —H | —H | |
| D-298 | 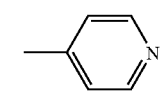 | —H | —H | |
| D-299 | 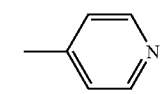 | —H | —H | |
| D-300 | 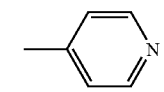 | —H | —H | |
| D-301 | —H | | —H | —H |
| D-302 | —H | | —H | —H |
| D-303 | —H | | —H | —H |
| D-304 | —H | | —H | —H |
| D-305 | —H | | —H | —H |
| D-306 | —H | | —H | —H |
| D-307 | —H | | —H | —H |
| D-308 | —H | | —H | —H |
| D-309 | —H | | —H | —H |
| D-310 | —H | | —H | —H |
| D-311 | —H | | —H | —H |
| D-312 | —H | | —H | —H |
| D-313 | —H | | —H | —H |
| D-314 | —H | | —H | —H |
| D-315 | —H | | —H | —H |
| D-316 | —H | | —H | —H |
| D-317 | —H | | —H | —H |
| D-318 | —H | | —H | —H |
| D-319 | —H | | —H | —H |
| D-320 | —H | | —H | —H |
| D-321 | —H | | —H | —H |
| D-322 | —H | | —H | —H |
| D-323 | —H | | —H | —H |
| D-324 | —H | | —H | —H |
| D-325 | —H | | —H | —H |
| D-326 | —H | | —H | —H |
| D-327 | —H | | —H | —H |
| D-328 | —H | | —H | —H |
| D-329 | —H | | —H | —H |
| D-330 | —H | | —H | —H |
| D-331 | 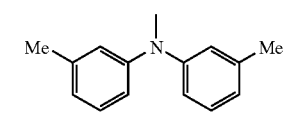 | —H | —H | |
| D-332 | 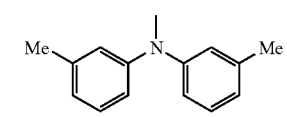 | —H | —H | |

-continued

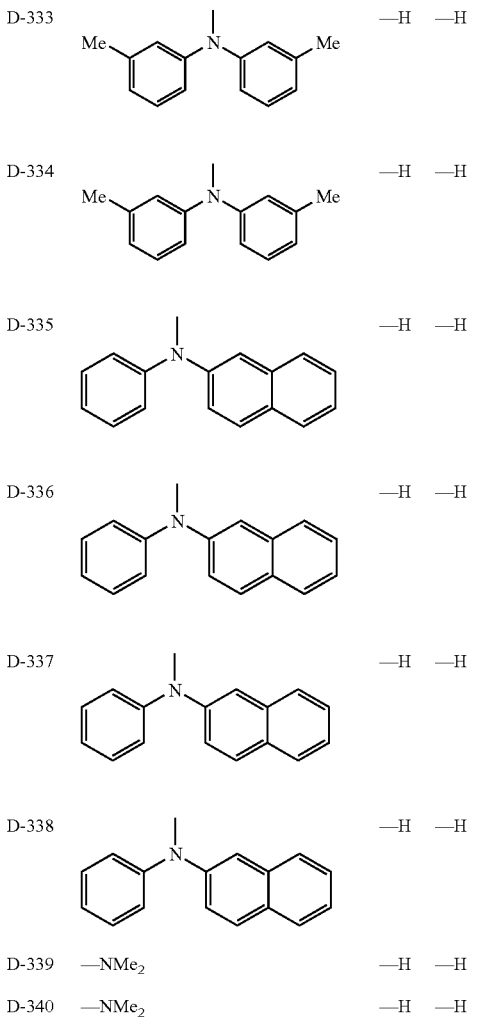

Next, the process for producing the aromatic amine derivatives of the present invention is described.

The process for producing the aromatic amine derivatives represented by the general formula (I) according to the present invention is not particularly limited, and the aromatic amine derivatives may be produced by known methods. For example, 2.8-dibromochrysene obtained by the method described in M. D. Bancia et al., "Rev. Roum. Chim.", 34, 1907(1989), is aminated in the presence of a diarylamine to produce the aromatic amine.

In the aromatic amine derivatives represented by the general formula (I) according to the present invention, since the two amino groups are bonded to the chrysene structure as a center of light emission, the association between the compounds is prevented, resulting in a prolonged life thereof. Further, the aromatic amine derivatives have a strong fluorescence in a solid state, and are excellent in field light emission, which leads to a fluorescent quantum efficiency as high as 0.3 or more. In addition, the aromatic amine derivatives of the present invention exhibit not only excellent capabilities of injecting and transporting holes from the metal electrode or organic thin film layers, but also excellent capabilities of injecting and transporting electrons from the metal electrode or organic thin film layers and, therefore, are usefully usable as light emitting materials for organic EL devices, in particular, as hole transporting materials and doping materials. Besides, the aromatic amine derivatives of the present invention may be used together with other hole transporting materials, electron transporting materials or doping materials.

The organic EL device of the present invention includes an anode, a cathode, and one or plural organic thin film layers sandwiched between the anode and the cathode. In the case where the one or plural organic thin film layers are of one layer type, a light emitting layer as the organic thin film layer is provided between the anode and the cathode. The light emitting layer contains the light emitting material and may further contain a hole injecting material or an electron injecting material in order to effectively transport holes injected from the anode or electrons injected from the cathode to the light emitting material. The aromatic amine derivatives according to the present invention have a high light emitting property and excellent hole injectability and hole transportability as well as excellent electron injectability and electron transportability and, therefore, can be used as a light emitting material or a doping material in the light emitting layer.

In the organic EL device of the present invention, the light emitting layer preferably contains the aromatic amine derivative of the present invention in an amount of usually 0.1 to 20% by weight and preferably 1 to 10% by weight. Further, the aromatic amine derivatives of the present invention exhibit not only an extremely high fluorescent quantum efficiency but also high hole transportability and electron transportability, and further are capable of forming a uniform thin film, so that the light emitting layer may be formed from the aromatic amine derivatives only.

On the other hand, in the case where the organic EL device of the present invention includes two or more organic thin film layers including at least the light emitting layer which are sandwiched between the cathode and anode, the organic thin film layers preferably include an organic layer containing the aromatic amine derivative as a main component which is disposed between the anode and the light emitting layer. Such an organic layer may be a hole injecting layer, a hole transporting layer, etc., and preferably contains the aromatic amine derivative of the present invention in the form of a single substance and a component of a mixture.

In addition, when the aromatic amine derivative of the present invention is used as a doping material, the light emitting layer of the organic EL device preferably further contains as a host material, at least one compound selected from the group consisting of an anthracene derivative represented by the following general formula (III), an anthracene derivative represented by the following general formula (IV) and a pyrene derivative represented by the following general formula (V):

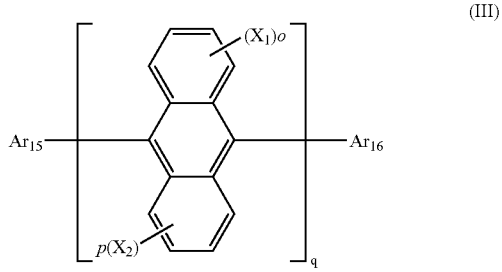

(III)

wherein $X_1$ and $X_2$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom;

o and p are each independently an integer of 0 to 4 with the proviso that o and/or p are respectively an integer of 2 or more, plural $X_1$ groups and/or plural $X_2$ groups are respectively the same or different;

$Ar_{15}$ and $Ar_{16}$ are each independently a substituted or unsubstituted aryl group having 5 to 50 ring carbon atoms, or a substituted or unsubstituted heterocyclic group having 5 to 50 ring carbon atoms with the proviso that at least one of $Ar_{15}$ and $Ar_{16}$ is a substituted or unsubstituted condensed ring aryl group having 10 to 50 ring carbon atoms or a substituted or unsubstituted aryl group having 10 or more ring carbon atoms; and q is an integer of 1 to 3 with the proviso that when q is an integer of 2 or more, the plural groups in the square bracket ([ ]) may be the same or different.

Specific examples of $X_1$ and $X_2$, and $Ar_{15}$ and $Ar_{16}$ as well as substituent groups which may be bonded thereto, are the same as those described above in the general formula (I).

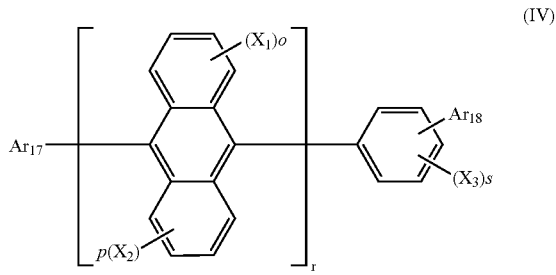

(IV)

wherein $X_1$ to $X_3$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom;

o, p and s are each independently an integer of 0 to 4 with the proviso that when o, p and s are respectively an integer of 2 or more, plural $X_1$ groups, plural $X_2$ groups and plural $X_3$ groups may be respectively the same or different;

$Ar_{17}$ is a substituted or unsubstituted condensed ring aryl group having 10 to 50 ring carbon atoms, and $Ar_{18}$ is a substituted or unsubstituted aryl group having 5 to 50 ring carbon atoms; and r is an integer of 1 to 3 with the proviso that when r is an integer of 2 or more, the plural groups in the square bracket ([ ]) may be the same or different.

Specific examples of $X_1$ to $X_3$, and $Ar_{17}$ and $Ar_{18}$ as well as substituent groups which may be bonded thereto, are the same as those described above in the general formula (I).

Specific examples of the anthracene derivatives represented by the general formulae (III) and (IV) include the following compounds, though not particularly limited to these exemplified compounds AN1
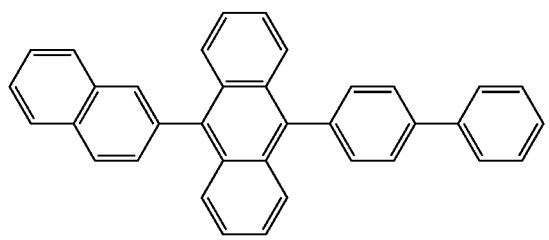
AN2
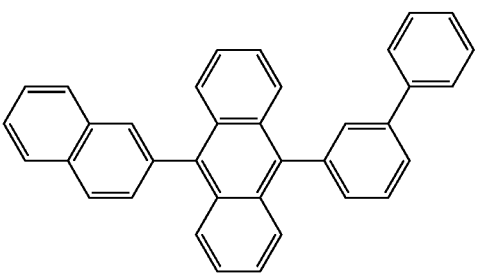
AN3
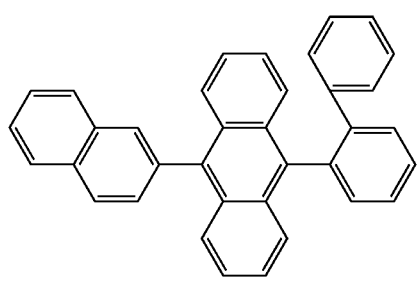
AN4
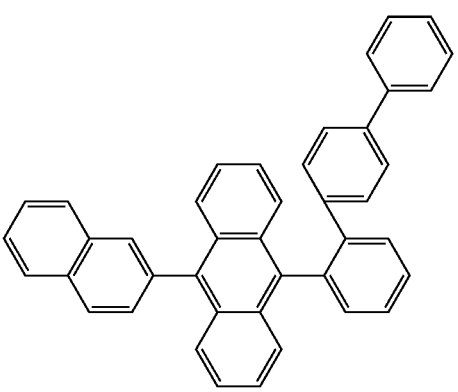
AN5
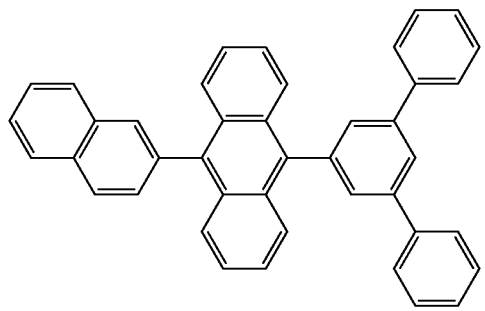
AN6
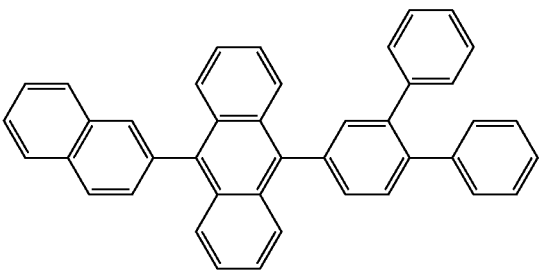
AN7
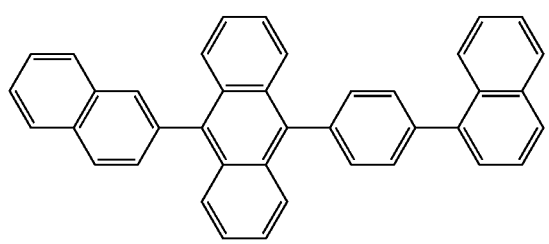
AN8
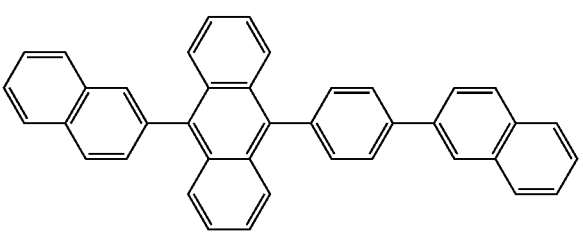
AN9
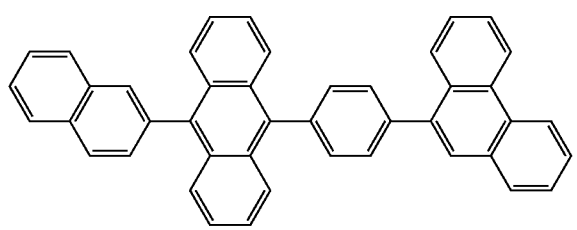
AN10
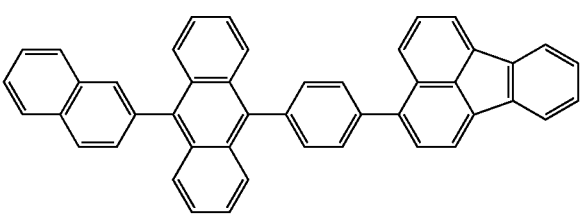

-continued
AN11
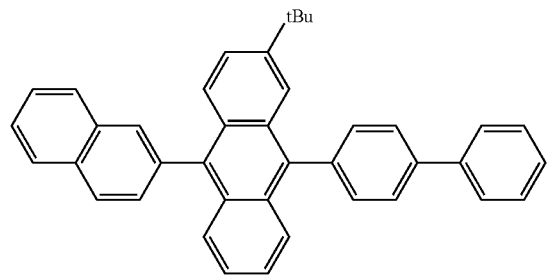
AN12
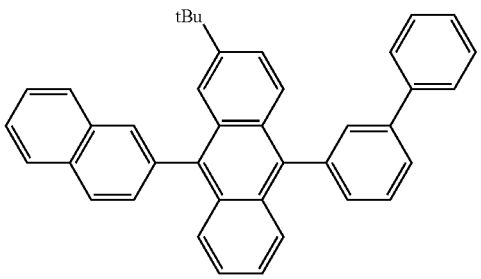
AN13
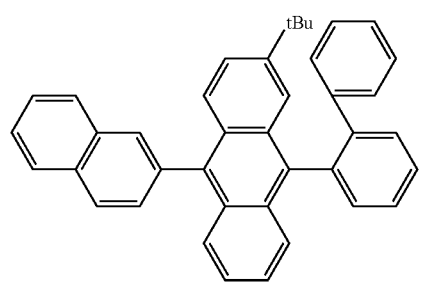
AN14
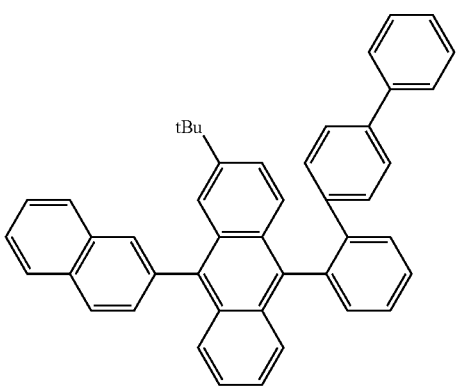
AN15
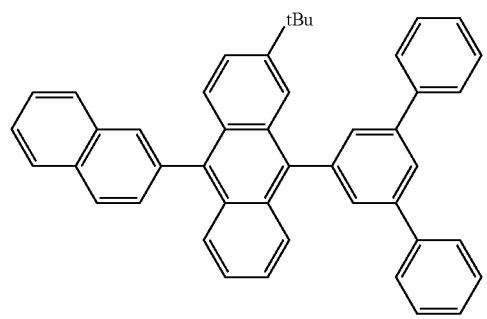
AN16
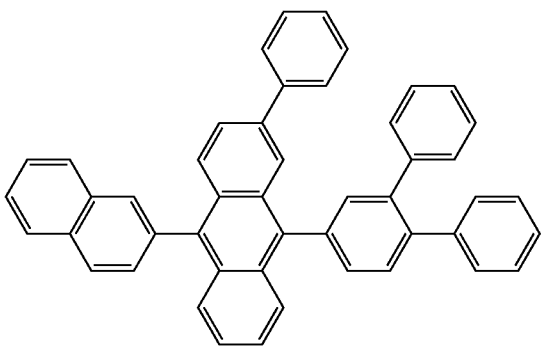
AN17
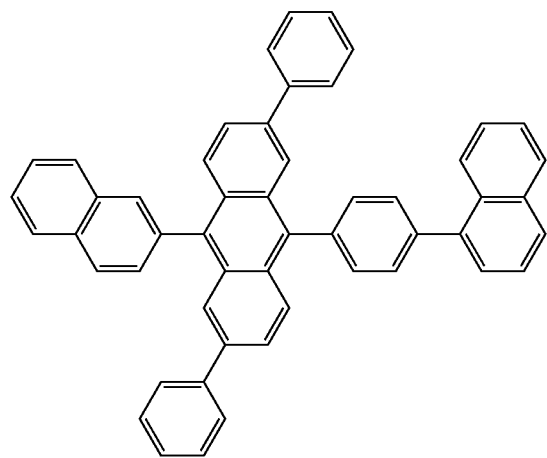
AN18
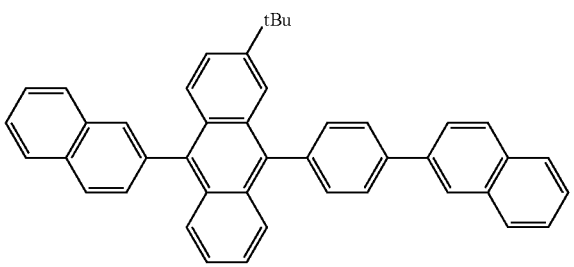

-continued
AN19
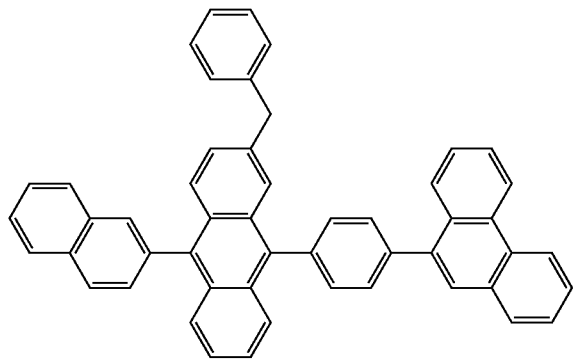
AN20
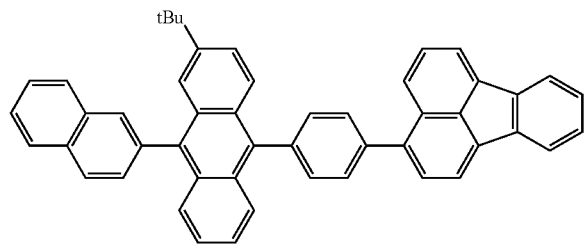
AN21
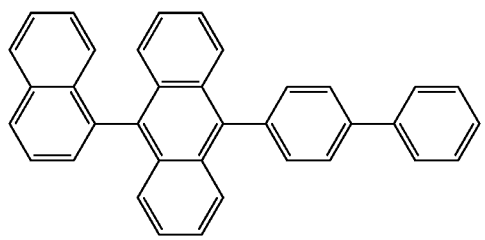
AN22
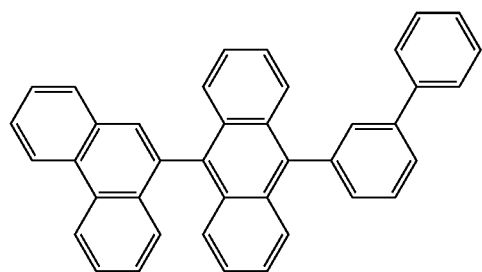
AN23
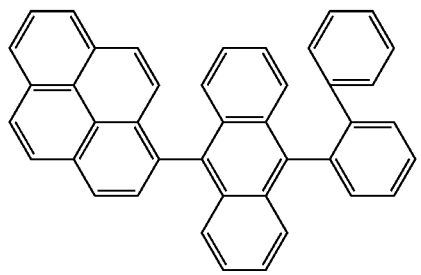
AN24
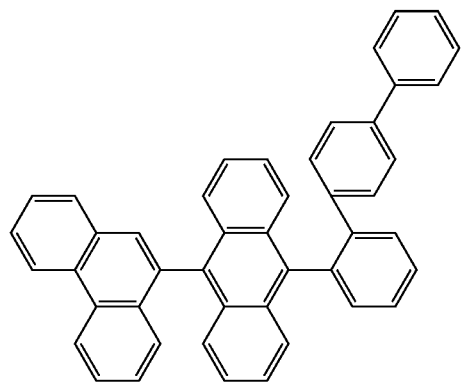
AN25
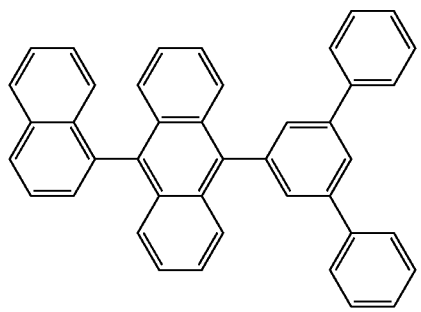
AN26
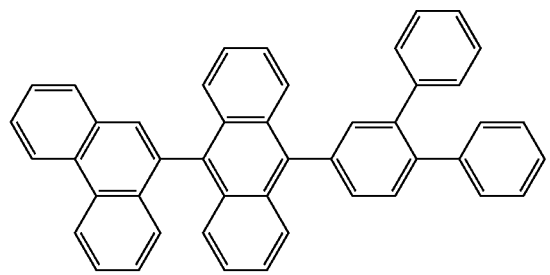
AN27
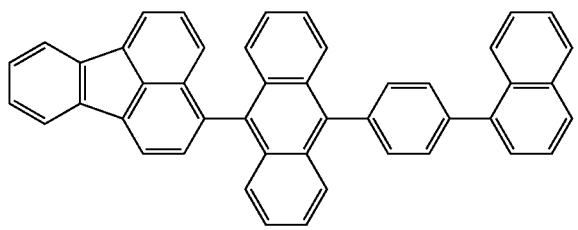
AN28
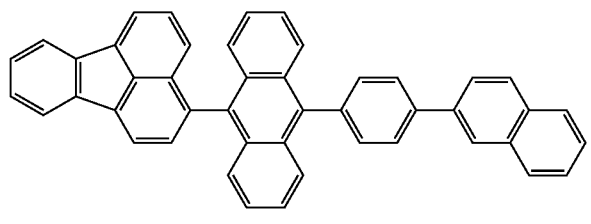

-continued
AN29
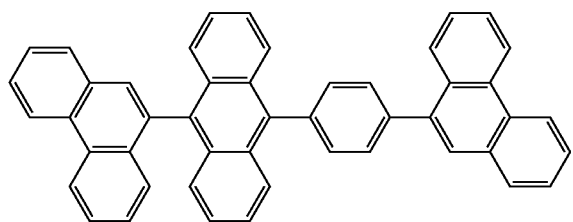
AN30
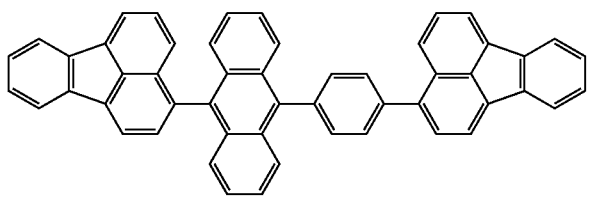
AN31
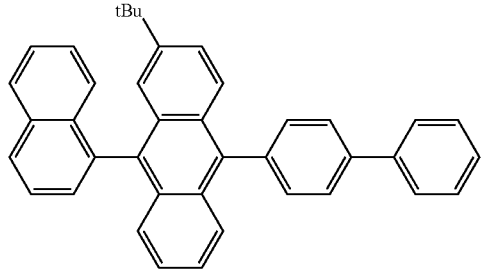
AN32
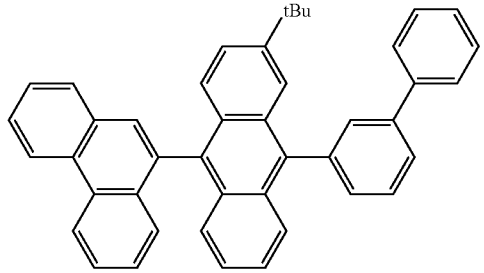
AN33
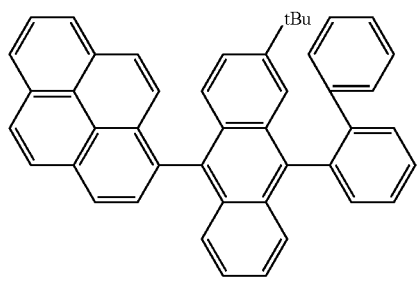
AN34
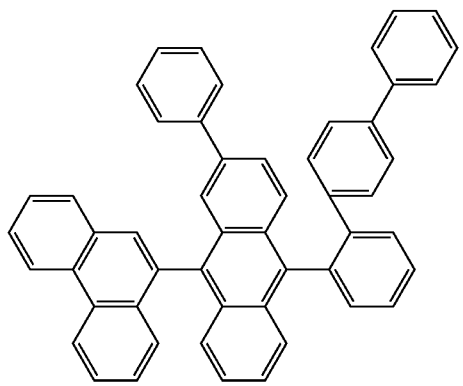
AN35
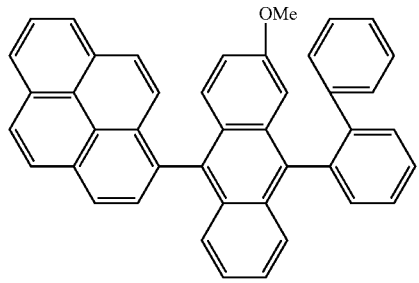
AN36
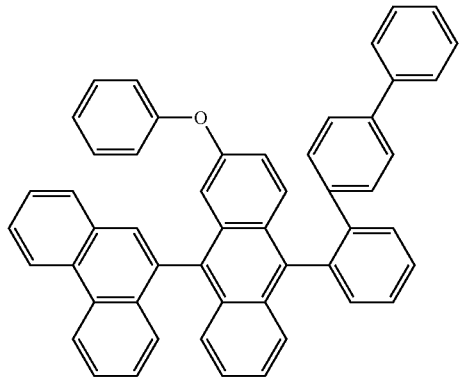
AN37
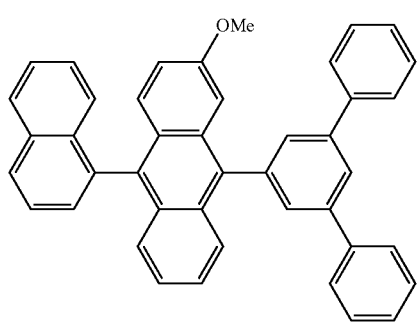
AN38
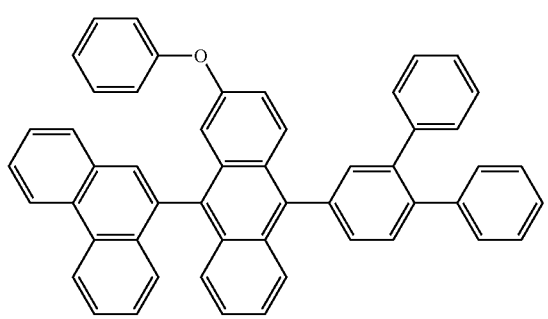

-continued
AN39
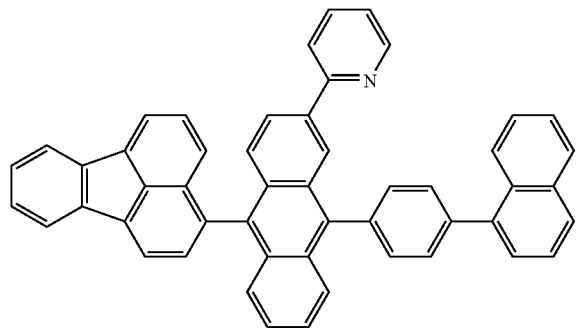
AN40
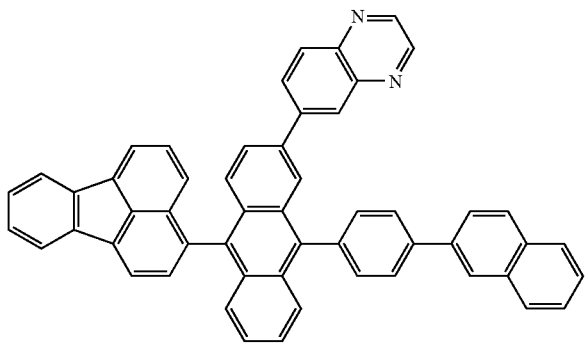
AN41
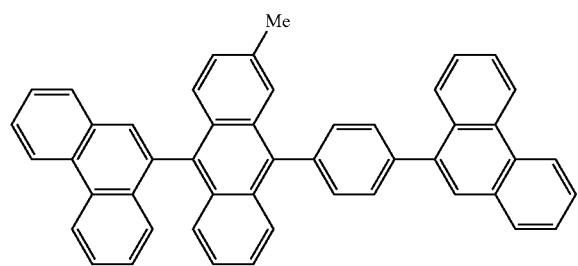
AN42
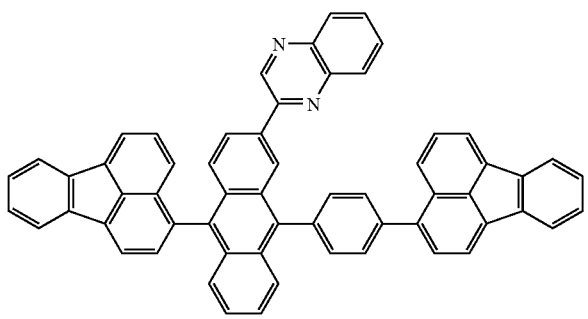
AN43
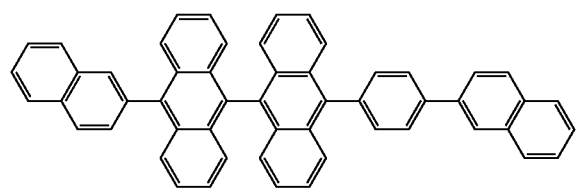
AN44
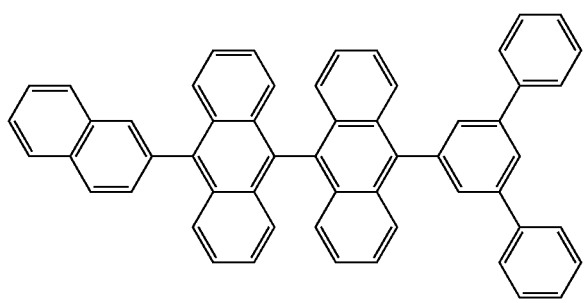
AN45
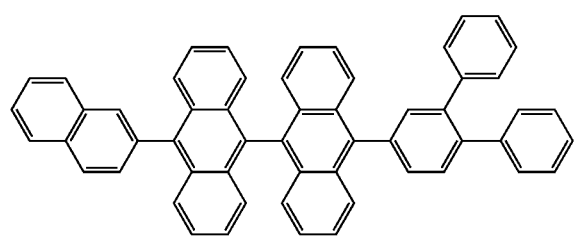
AN46
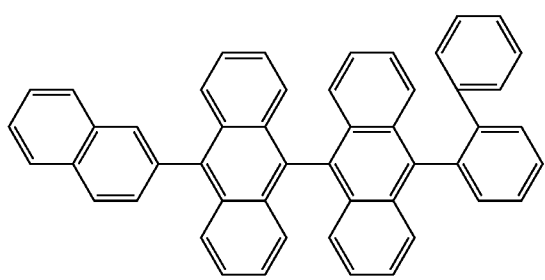

-continued

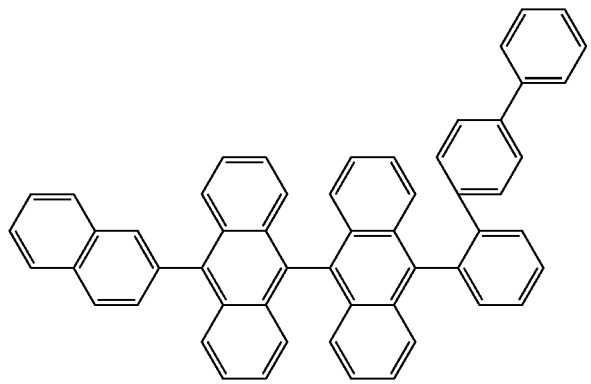

AN47

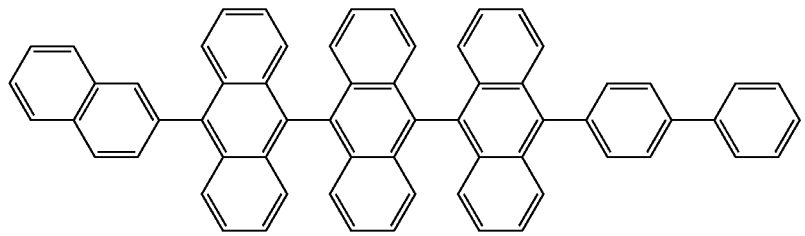

AN48

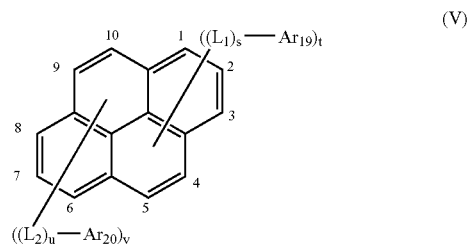

(V)

wherein Ar$_{19}$ and Ar$_{20}$ are each independently a substituted or unsubstituted aryl group having 5 to 50 ring carbon atoms;

L$_1$ and L$_2$ are respectively a substituted or unsubstituted phenylene group, a substituted or unsubstituted naphthalenylene group, a substituted or unsubstituted fluorenylene group or a substituted or unsubstituted dibenzosilolylene group;

s is an integer of 0 to 2, t is an integer of 1 to 4, u is an integer of 0 to 2, and v is an integer of 1 to 4; and L$_1$ or Ar$_{19}$ is bonded to any of 1- to 5-positions of the pyrene ring, and L$_2$ or Ar$_{20}$ is bonded to any of the 6- to 10-positions of the pyrene ring; and with the proviso that when a sum of t and v (t+v) is an even number, Ar$_{19}$, Ar$_{20}$, L$_1$ and L$_2$ satisfy the following conditions (1) or (2):

(1) Ar$_{19}$ and Ar$_{20}$ are different groups from each other, and/or L$_1$ and L$_2$ are different groups from each other, or (2) when Ar$_{19}$ and Ar$_{20}$ are the same group, and L$_1$ and L$_2$ are the same group, (2-1) s is unequal to u (s≠u), and/or t is unequal to v (t≠v), or (2-2) when s is equal to u (s=u) and t is equal to v (t=v), (2-2-1) L$_1$ and L$_2$, or the pyrene ring, are respectively bonded to different positions of Ar$_{19}$ and Ar$_{20}$, or (2-2-2) when L$_1$ and L$_2$, or the pyrene ring, are respectively bonded to the same positions of Ar$_{19}$ and Ar$_{20}$, L$_1$ and L$_2$, or Ar$_{19}$ and Ar$_{20}$ as substituent groups are bonded to positions of the pyrene ring other than the 1- and 6-positions or the 2- and 7-positions thereof.

Specific examples of Ar$_{19}$ and Ar$_{20}$, and L$_1$ and L$_2$ as well as substituent groups which may be bonded thereto, are the same as those described above in the general formula (I).

Specific examples of the pyrene derivatives represented by the general formula (V) include the following compounds, though not particularly limited to these exemplified compounds.

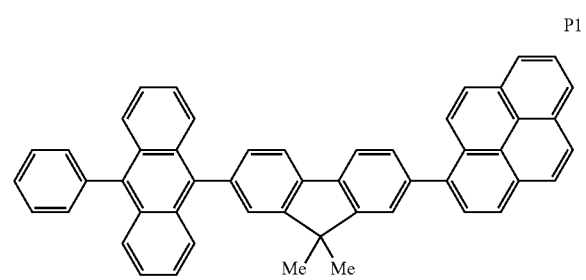

P1

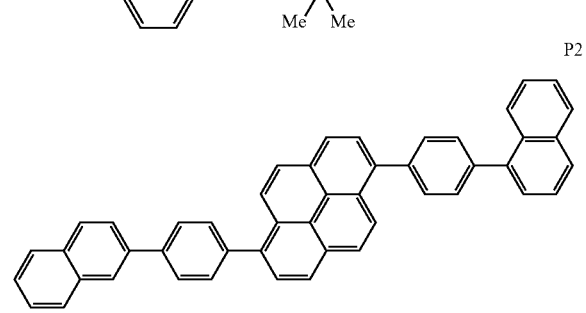

P2

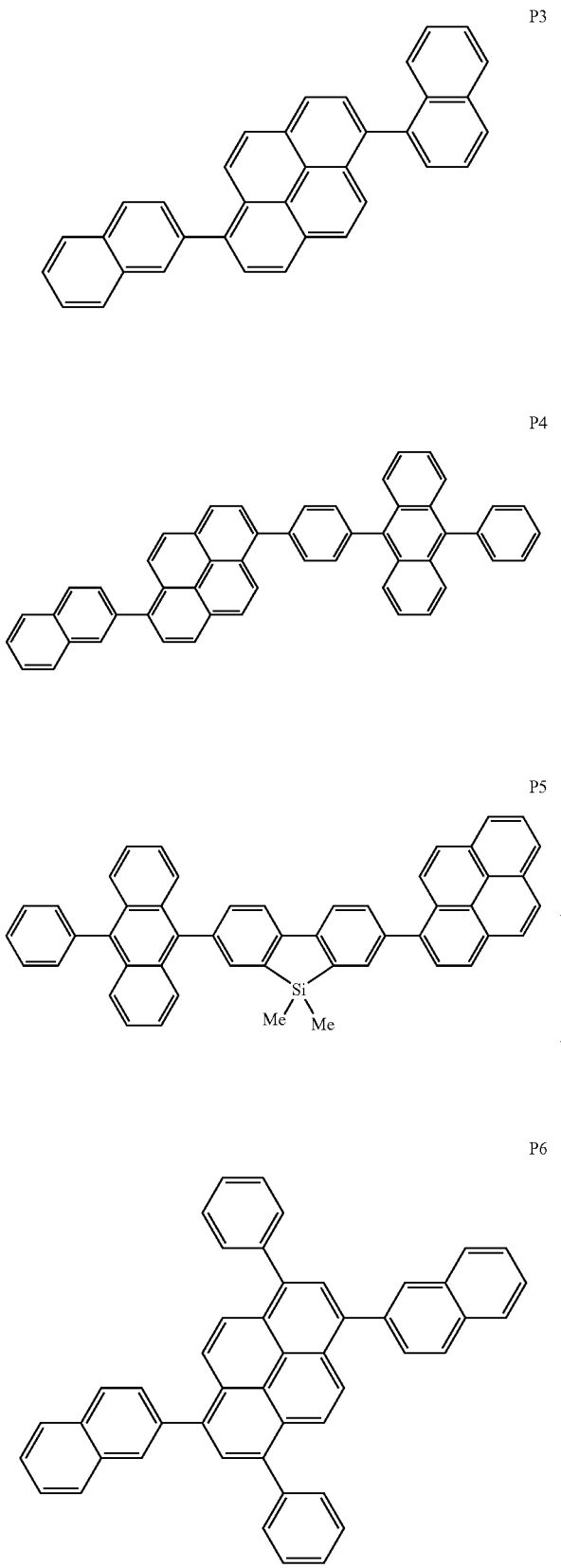
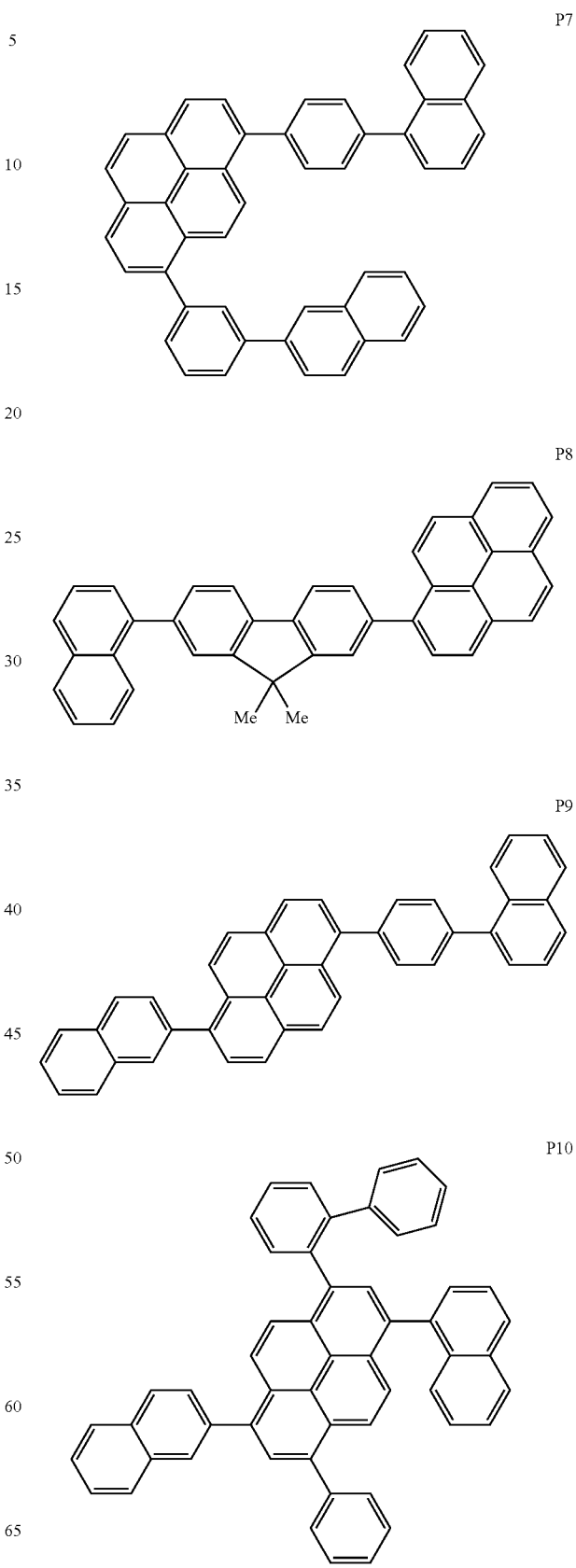

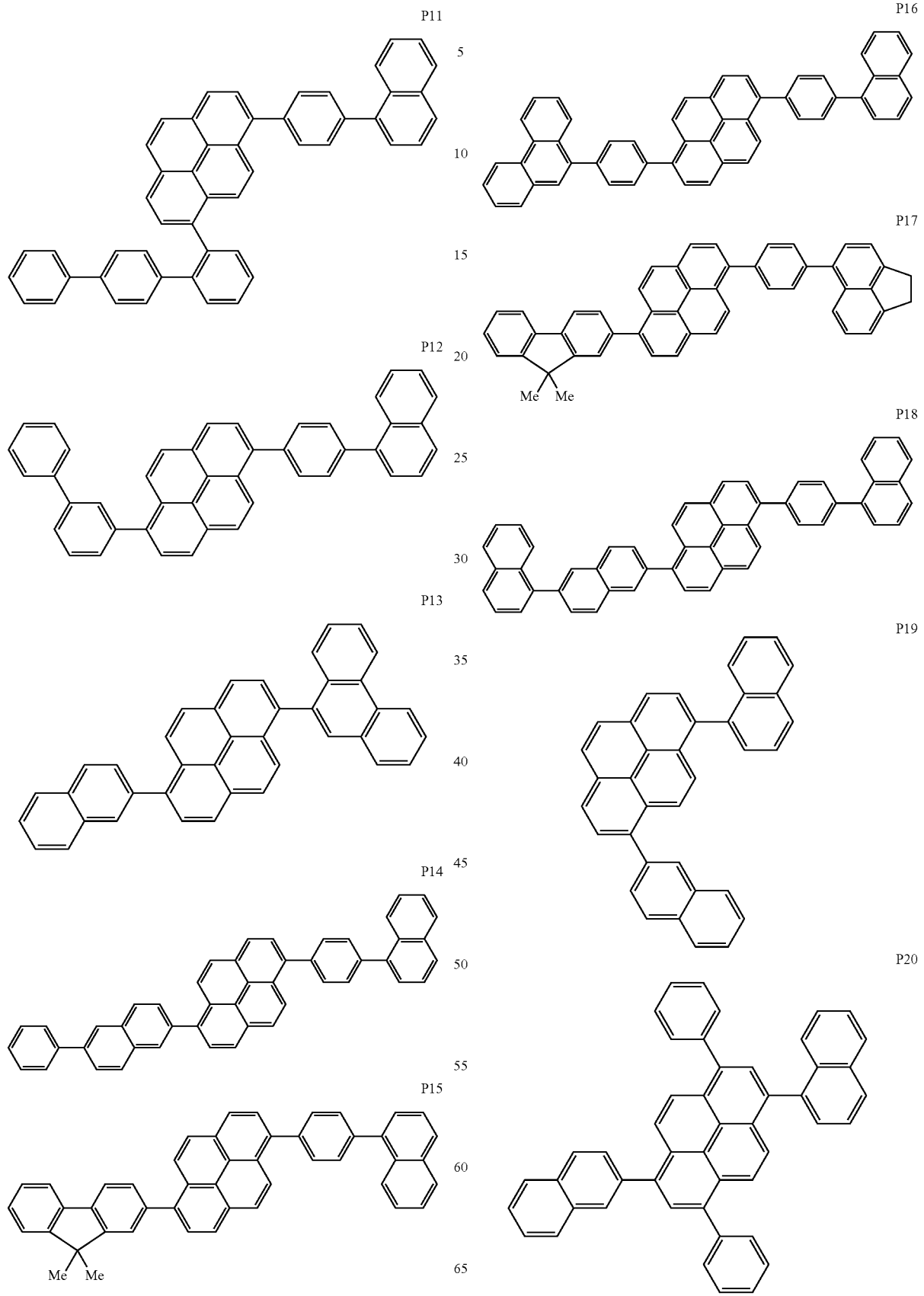

-continued

P21

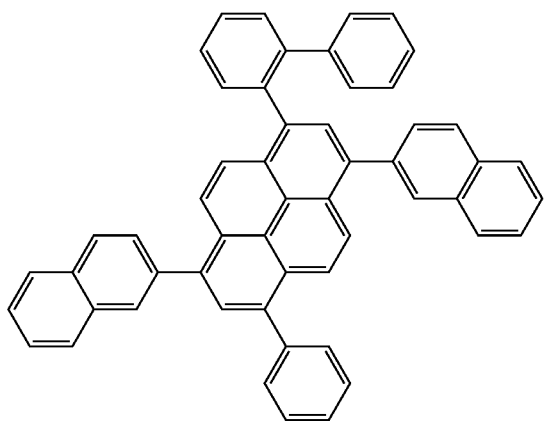

Examples of the organic EL device having plural organic thin film layers include those having a multilayer structure such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The respective plural organic thin film layers may also optionally contain, in addition to the aromatic amine derivatives of the present invention, conventionally known light emitting materials, doping materials, hole injecting materials and electron injecting materials according to requirements. The organic EL device having such plural organic thin film layers can be prevented from suffering from deterioration in luminance and service life due to quenching. If required, the light emitting materials, doping materials, hole injecting materials and electron injecting materials may be used in combination with each other. The use of the doping materials enables the resultant device to be improved in luminance of light emitted and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may be constituted from a hole injecting layer into which holes are injected from the electrode, and a hole transporting layer for accepting the holes from the hole injecting layer and transporting the holes to the light emitting layer. Also, the multi-layer electron injecting layer may be constituted from an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the other organic thin film layers or the metal electrodes.

Examples of the host material or doping material other than the compounds represented by the above general formulae (III) to (V) that is usable in the light emitting layer together with the aromatic amine derivatives of the present invention include condensed polycyclic aromatic compounds such as naphthalene, phenanthrene, rubrene, anthracene, tetracene, pyrene, perylene, chrysene, decacyclene, coronene, tetraphenyl cyclopentadiene, pentaphenyl cyclopentadiene, fluorene, spirofluorene, 9,10-diphenyl anthracene, 9,10-bis(phenylethynyl)anthracene and 1,4-bis(9'-ethynylanthracenyl)benzene, and derivatives thereof; organometallic complexes such as tris(8-quinolinolato)aluminum and bis-(2-methyl-8-quinolinolato)-4-(phenylphenolato)aluminum; triarylamine derivatives; styrylamine derivatives; stilbene derivatives; coumarin derivatives; pyrane derivatives; oxazoline derivatives; benzothiazole derivatives; benzooxazole derivatives; benzoimidazole derivatives; pyrazine derivatives; cinnamic ester derivatives; diketo-pyrrolopyrrole derivatives; acridone derivatives; and quinacridone derivatives, though not particularly limited thereto.

The hole injecting material is preferably made of compounds which have a good hole transportability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazole thione, pyrazoline, pyrazolone, tetrahydroimidazole, hydrazone, acyl hydrazone, polyaryl alkanes, stilbene, butadiene, benzidine-type triphenylamine, styrylamine-type triphenylamine, diamine-type triphenylamine and derivatives thereof, as well as polyvinyl carbazoles, polysilanes, and polymer materials such as conductive polymers, though not particularly limited thereto.

Of these hole injecting materials usable in the organic EL device of the present invention, more effective hole injecting materials are aromatic tertiary amine derivatives and phthalocyanine derivatives.

Specific examples of the aromatic tertiary amine derivatives include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc—O—GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, for example, the above hole transporting layer or hole injecting layer.

The electron injecting material is preferably made of compounds which have a good electron transportability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinlodimethane, diphenoquinone, thiopyrane dioxide, oxazole, oxadiazole, triazole, imidazole, perylenetetracarboxylic acid, fluorenylidene methane, anthrone, and derivatives thereof, though not particularly limited thereto. Further, an electron accepting substance and an electron donating substance may be added to the hole injecting material and the electron injecting material, respectively, for enhancing sensitization thereof.

In the organic EL device of the present invention, among these electron injecting materials, more effective electron injecting materials are metal complex compounds and nitrogen-containing five-membered ring derivatives.

Specific examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, and bis(2-methyl-8-quinolinato) (2-naphtholato) gallium, though not particularly limited thereto.

Examples of the preferred nitrogen-containing five-membered ring derivatives include derivatives of oxazole, thiazole, oxadiazole, thiadiazole or triazole. Specific examples of the nitrogen-containing five-membered ring derivatives include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain, in addition to at least one aromatic amine derivative selected from those compounds represented by the general formula (I), at least one material selected from the group consisting of light emitting materials, doping materials, hole injecting materials and electron injecting materials. The organic EL device of the present invention may be further provided on a surface thereof with a protective layer, or the whole part thereof may be protected with silicone oil, resins, etc., in order to enhance a stability thereof against temperature, humidity, atmosphere, etc.

The anode of the organic EL device according to the present invention may be suitably made of a conductive material having a work function more than 4 eV. Examples of the conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic conductive resins such as polythiophene and polypyrrole. The cathode of the organic EL device according to the present invention may be suitably made of a conductive material having a work function of 4 eV or less. Examples of the conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon temperature of vapor deposition sources, atmosphere, vacuum degree, etc. The anode and the cathode may be respectively constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is produced from the above conductive material by vapor deposition method, sputtering method, etc., so as to ensure a desirable transparency thereof. The electrode disposed on a light emitting surface of the device preferably has a light transmittance of 10% or more. The substrate is not particularly limited as long as it has a good mechanical and thermal strength as well as a good transparency. Examples of the substrate include glass substrates and transparent resin films. Specific examples of the transparent resin films include films made of polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyesters, polycarbonates, polyurethanes, polyimides, and polyether imides.

The respective layers of the organic EL device of the present invention may be formed by either a dry film-forming method such as vacuum deposition, sputtering, plasma and ion-plating, or a wet film-forming method such as spin-coating, dipping and flow-coating. The thickness of the respective layers is not particularly limited, but should be adjusted to an appropriate range. If the thickness is too large, a large electric voltage must be applied to the device in order to achieve a predetermined light output, resulting in a poor efficiency of light emission. On the other hand, if the thickness is too small, pinholes tend to be formed in the layers, thereby failing to obtain a sufficient luminance of light emitted even upon applying an electric field thereto. The suitable thickness of the respective layers is usually in the range of from 5 nm to 10 μm and preferably from 10 nm to 0.2 μm.

In the wet film-forming method, materials forming the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for the purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethyl methacrylate, polymethyl acrylate and celluloses as well as copolymers thereof, photoconductive resins such as poly-N-vinyl carbazole and polysilanes, and conductive resins such as polythiophene and polypyrrole. Examples of the additives include antioxidants, ultraviolet absorbers and plasticizers.

The organic EL device of the present invention is suitably applied to, for example, surface light-emitting members such as flat display panels for wall-type televisions, light sources for copiers, printers, back light for liquid crystal displays and measuring equipments, display panels, marker light, etc. Further, the material of the present invention can be used not only for organic EL devices but also in other applications such as electrophotographic members, photoelectric converters, solar cells, image sensors, etc.

EXAMPLES

Next, the present invention is described in more detail by reference to the following examples.

Synthesis Example 1

Synthesis of Compound (D-107)

(1) Synthesis of 3,4-bis[(trimethylsilyl)oxy]-1,6-bis(m-methoxybenzyl)-3-hexene

Under an argon gas flow, 73 g (3.18 mol) of sodium and 2 L of toluene were charged into a 5 L glass flask equipped with a condenser, and then heated to 110° C. to melt the sodium. Successively, 206 g (1.06 mol) of methyl 3-(m-methoxyphenyl)propionate and 346 g (3.18 mol) of trimethylsilyl chloride were added to the flask, and the contents of the flask were stirred at 110° C. for 20 h. After completion of the reaction, the precipitated inorganic salts were separated from the reaction solution by filtration. The organic layer thus separated was washed with 1 L of water four times and then dried with magnesium sulfate. The resultant dried product was concentrated under reduced pressure to obtain a crude product. The thus obtained crude product (210 g) was directly used in the subsequent reaction.

(2) Synthesis of 2,8-dimethoxy-5,6,11,12-tetrahydrochrysene

Under an argon gas flow, 210 g (0.44 mol) of 3,4-bis[(trimethylsilyl)oxy]-1,6-bis(m-methoxybenzyl)-3-hexene and 2 kg of polyphosphoric acid were charged into a 5 L glass flask equipped with a condenser, and then stirred at room temperature for 2 h. After completion of the reaction, 2 L of water and 1 L of toluene were added to the flask to extract an organic layer from the reaction solution. The organic layer thus extracted was concentrated under reduced pressure, and the resultant crude crystal was recrystallized with toluene, thereby obtaining 75 g of the aimed product (yield: 57%; a diastereomer).

(3) Synthesis of 2,8-dimethoxychrysene

Under an argon gas flow, 70 g (0.24 mol) of 2,8-dimethoxy-5,6,11,12-tetrahydrochrysene and 50 g of Pd/C were charged into a 5 L round bottom flask equipped with a condenser, and heated at 200° C. for 1 h. Thereafter, the obtained reaction mixture was heated to 300° C. and sublimated. The resultant reaction product was recrystallized with acetic acid, thereby obtaining 24 g of the aimed product (yield: 35%).

(4) Synthesis of chrysene-2,8-diol

Under an argon gas flow, 24 g (0.083 mol) of 2,8-dimethoxychrysene and 2 L of methylene chloride were charged into a 3 L glass flask equipped with a condenser, and cooled to −60° C. Successively, 4.1 g (0.17 mol) of boron tribromide was slowly dropped into the flask, and then the contents of the flask were stirred at room temperature for 18 h. After completion of the reaction, 1 L of water was added to the flask to separate an organic layer from the reaction solution. The resultant crude crystal was short-passed through silica gel (using THF (tetrahydrofuran) as a developing solvent). The obtained product was concentrated under reduced pressure, and the resultant crude product (25 g) was directly used in the subsequent reaction.

(1-5) Synthesis of chrysene-2,8-trifluoromethane sulfonate

Under an argon gas flow, 25 g (0.083 mol) of chrysene-2,8-diol, 16.7 g (0.17 mol) of diisopropylamine and 400 mL of methylene chloride were charged into a 1 L glass flask equipped with a condenser, and cooled to 0° C. Successively, 47 g (0.17 mol) of trifluoromethanesulfonic anhydride was slowly dropped into the flask, and then the contents of the flask were stirred at room temperature for 18 h. After completion of the reaction, 400 mL of water was added to the flask to separate an organic layer from the reaction solution. The resultant crude crystal was purified by silica gel chromatography (using toluene as a developing solvent), thereby obtaining 26 g of the aimed product (yield: 60%).

(1-6) Synthesis of Compound (D-107)

Under an argon gas flow, 5.2 g (10 mmol) of chrysene-2,8-trifluoromethane sulfonate, 6.7 g (25 mmol) of di(2-naphthyl)amine, 0.03 g (1.5 mol %) of palladium acetate, 0.08 g (3 mol %) of 2-(di-t-butylphosphino)biphenyl, 2.4 g (25 mmol) of t-butoxy sodium and 100 mL of dried toluene were charged into a 300 mL three-necked flask equipped with a condenser, and the contents of the flask were stirred under heating at 100° C. over night. After completion of the reaction, the precipitated crystal was separated from the reaction solution by filtration, and washed with 50 mL of toluene and 100 mL of methanol, thereby obtaining 4.5 g of a light yellow powder. As a result of measurements of $^1$H-NMR spectrum (refer to FIG. 1 and Table 1) and FD-MS (field desorption mass spectrum), the thus obtained powder was identified to be the compound (D-107) (yield: 60%). Meanwhile, the $^1$H-NMR spectrum was measured by "DRX-500" available from Brucker Inc., using a heavy methylene chloride solvent. The thus obtained compound exhibited a maximum absorption wavelength of 385 nm and a maximum fluorescent wavelength of 428 nm as measured in a toluene solution thereof.

TABLE 1

| No. | Position (ppm) | Height (%) |
|---|---|---|
| 1 | 0.07937 | 0.347 |
| 2 | 0.1506 | 0.201 |
| 3 | 1.26255 | 0.313 |
| 4 | 1.52793 | 100 |
| 5 | 2.11921 | 0.205 |
| 6 | 7.23706 | 0.314 |
| 7 | 7.32153 | 0.775 |
| 8 | 7.32847 | 0.68 |
| 9 | 7.33099 | 0.736 |
| 10 | 7.33666 | 0.767 |
| 11 | 7.34423 | 0.893 |
| 12 | 7.34884 | 0.792 |
| 13 | 7.36187 | 0.647 |
| 14 | 7.40852 | 2.486 |
| 15 | 7.42365 | 3.283 |
| 16 | 7.4413 | 2.185 |
| 17 | 7.45706 | 1.2 |
| 18 | 7.47219 | 0.744 |
| 19 | 7.57052 | 1.229 |
| 20 | 7.58691 | 1.57 |
| 21 | 7.61339 | 1.637 |
| 22 | 7.69281 | 0.737 |

TABLE 1-continued

| No. | Position (ppm) | Height (%) |
|---|---|---|
| 23 | 7.70794 | 1.244 |
| 24 | 7.7237 | 1.053 |
| 25 | 7.73378 | 0.823 |
| 26 | 7.76026 | 1.179 |
| 27 | 7.76467 | 1.159 |
| 28 | 7.77035 | 1.142 |
| 29 | 7.77728 | 1.154 |
| 30 | 7.81636 | 3.174 |
| 31 | 7.83338 | 3.063 |
| 32 | 7.67877 | 0.388 |
| 33 | 7.8939 | 0.384 |
| 34 | 8.03194 | 0.28 |
| 35 | 8.57279 | 1.71 |
| 36 | 8.59107 | 1.62 |
| 37 | 8.64591 | 0.781 |
| 38 | 8.66356 | 0.787 |

INDUSTRIAL APPLICABILITY

As described in detail above, the organic EL device using the aromatic amine derivative according to the present invention can exhibit a practically sufficient luminance of light emitted even upon applying a low electric voltage thereto, and has a high efficiency of light emission, and the device is free from deterioration in properties even after being used for a long period of time and, therefore, has a long life. Thus, the organic EL device is useful as a surface light-emitting member for wall-type televisions or a light source such as a backlight for displays.

The invention claimed is:

1. An aromatic amine derivative represented by the following general formula (I):

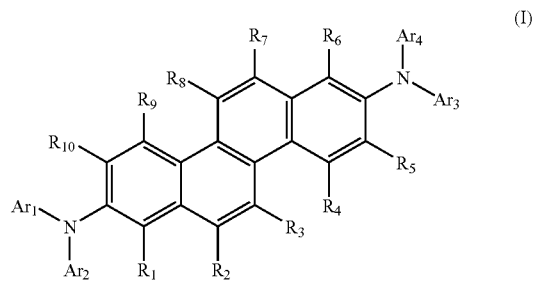

wherein $R_1$ to $R_{10}$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms; and $Ar_1$ to $Ar_4$ are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, or a substituted or unsubstituted heterocyclic group having 5 to 50 ring carbon atoms, with the proviso that when $Ar_1$ to $Ar_4$ are aryl groups, $Ar_1$ and $Ar_2$, and $Ar_3$ and $Ar_4$ may be respectively bonded to each other to form a saturated or unsaturated ring.

2. The aromatic amine derivative according to claim 1, wherein $R_2$ and/or $R_7$ in the general formula (I) are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms.

3. The aromatic amine derivative according to claim 1, wherein $R_3$ and/or $R_8$ in the general formula (I) are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms.

4. The aromatic amine derivative according to claim 1, which is represented by the following general formula (II):

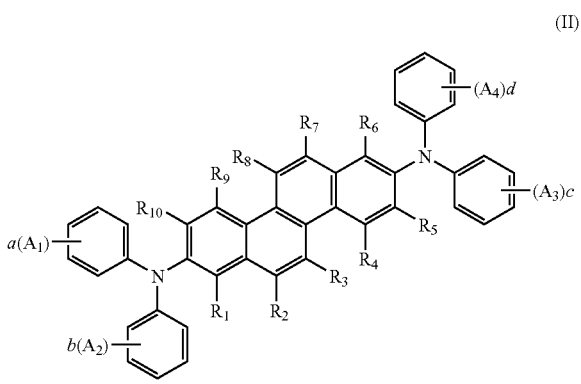

wherein $R_1$ to $R_{10}$ are each independently the same as those of the general formula (I) as defined in claim 1;

$A_1$ to $A_4$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, a substituted or unsubstituted heterocyclic group having 5 to 50 ring carbon atoms, or a halogen atom; and a, b, c and d are each independently an integer of 0 to 5, with the proviso that when a, b, c and d are respectively an integer of 2 or more, plural groups of each of $A_1$ to $A_4$ may be the same or different and bonded to each other to form a saturated or unsaturated ring; and $A_1$ and $A_2$, and $A_3$ and $A_4$ may be respectively bonded to each other to form a saturated or unsaturated ring.

5. The aromatic amine derivative according to claim 4, wherein $R_2$ and/or $R_7$ in the general formula (II) are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms.

6. The aromatic amine derivative according to claim 4, wherein $R_3$ and/or $R_8$ in the general formula (II) are each independently a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 ring carbon atoms.

7. An organic electroluminescent device comprising a cathode, an anode and, therebetween, a light emitting layer wherein the light emitting layer comprises at least one aromatic amine derivative as defined in claim 1.

8. An organic electroluminescent device comprising a cathode, an anode and, therebetween, a hole transporting layer, wherein the hole transporting layer comprises at least one aromatic amine derivative as defined in claim 1.

9. The organic electroluminescent device according to claim 7, wherein the light emitting layer comprises the aromatic amine derivative in an amount of 0.1 to 20% by weight.

10. The organic electroluminescent device according to claim 7, wherein the light emitting layer comprises the aromatic amine derivative as a doping material, and further comprises as a host material, an anthracene derivative represented by the following general formula (III):

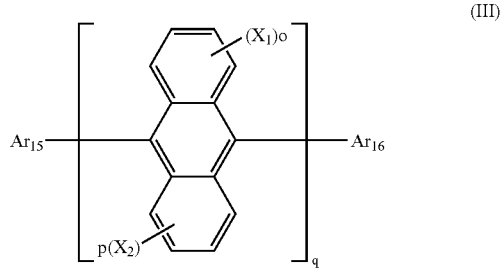

wherein $X_1$ and $X_2$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom;

o and p are each independently an integer of 0 to 4 with the proviso that o and/or p are respectively an integer of 2 or more, plural $X_1$ groups and/or plural $X_2$ groups are respectively the same or different;

$Ar_{15}$ and $Ar_{16}$ are each independently a substituted or unsubstituted aryl group having 5 to 50 ring carbon atoms, or a substituted or unsubstituted heterocyclic group having 5 to 50 ring carbon atoms with the proviso that at least one of $Ar_{15}$ and $Ar_{16}$ is a substituted or unsubstituted condensed ring aryl group having 10 to 50 ring carbon atoms or a substituted or unsubstituted aryl group having 10 or more ring carbon atoms; and q is an integer of 1 to 3 with the proviso that when q is an integer of 2 or more, the plural groups in the square bracket ([ ]) may be the same or different.

11. The organic electroluminescent device according to claim 9, wherein the light emitting layer comprises the aromatic amine derivative as a doping material, and further comprises as a host material, an anthracene derivative represented by the following general formula (IV):

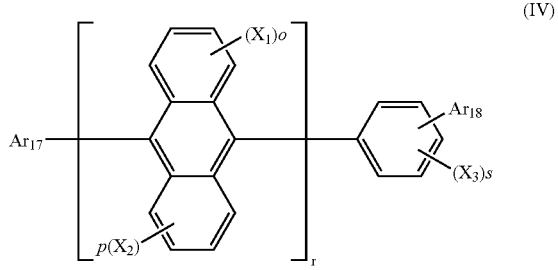

wherein $X_1$ to $X_3$ are each independently a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxy group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom;

o, p and s are each independently an integer of 0 to 4 with the proviso that when o, p and s are respectively an integer of 2 or more, plural $X_1$ groups, plural $X_2$ groups and plural $X_3$ groups may be respectively the same or different;

$Ar_{17}$ is a substituted or unsubstituted condensed ring aryl group having 10 to 50 ring carbon atoms, and $Ar_{18}$ is a substituted or unsubstituted aryl group having 5 to 50 ring carbon atoms; and r is an integer of 1 to 3 with the proviso that when r is an integer of 2 or more, the plural groups in the square bracket ([ ]) may be the same or different.

12. The organic electroluminescent device according to claim 7, wherein the light emitting layer comprises the aromatic amine derivative as a doping material, and further comprises as a host material, a pyrene derivative represented by the following general formula (V):

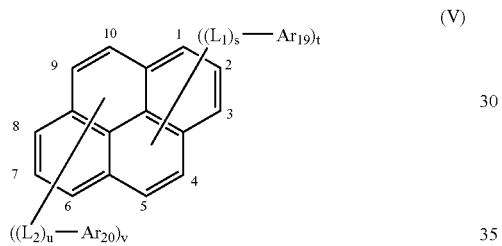

(V)

wherein $Ar_{19}$ and $Ar_{20}$ are each independently a substituted or unsubstituted aryl group having 5 to 50 ring carbon atoms;

$L_1$ and $L_2$ are respectively a substituted or unsubstituted phenylene group, a substituted or unsubstituted naphthalenylene group, a substituted or unsubstituted fluorenylene group, or a substituted or unsubstituted dibenzosilolylene group;

s is an integer of 0 to 2, t is an integer of 1 to 4, u is an integer of 0 to 2, and v is an integer of 1 to 4; and $L_1$ or $Ar_{19}$ is bonded to any of the 1- to 5-positions of the pyrene ring, and $L_2$ or $Ar_{20}$ is bonded to any of the 6- to 10-positions of the pyrene ring, with the proviso that when a sum of t and v (t+v) is an even number, $Ar_{19}$, $Ar_{20}$, $L_1$ and $L_2$ satisfy the following conditions (1) or (2):

(1) $Ar_{19}$ and $Ar_{20}$ are different groups from each other, and/or $L_1$ and $L_2$ are different groups from each other, or (2) when $Ar_{19}$ and $Ar_{20}$ are the same group, and $L_1$ and $L_2$ are the same group, (2-1) s is unequal to u (s≠u), and/or t is unequal to v (t≠v), or (2-2) when s is equal to u (s=u) and t is equal to v (t=

(2-2-1) $L_1$ and $L_2$, or the pyrene ring, are respectively bonded to different positions of $Ar_{19}$ and $Ar_{20}$, or (2-2-2) when $L_1$ and $L_2$, or the pyrene ring, are respectively bonded to the same positions of $Ar_{19}$ and $Ar_{20}$, $L_1$ and $L_2$, or $Ar_{19}$ and $Ar_{20}$ as substituent groups are bonded to positions of the pyrene ring other than the 1- and 6-positions or the 2- and 7-positions thereof.

13. The aromatic amine derivative as claimed in claim 1, wherein $R_1$ to $R_{10}$ are each a hydrogen atom and $Ar_1$ to $Ar_4$ are each a group of the formula:

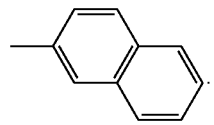

14. The organic electroluminescent device according to claim 7, wherein $R_1$ to $R_{10}$ are each a hydrogen atom and $Ar_1$ to $Ar_4$ are each a group of the formula:

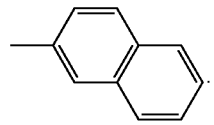

15. The organic electroluminescent device according to claim 8, wherein $R_1$ to $R_{10}$ are each a hydrogen atom and $Ar_1$ to $Ar_4$ are each a group of the formula:

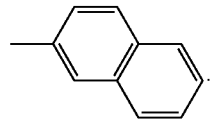

* * * * *